United States Patent
Eggers et al.

(10) Patent No.: US 6,623,454 B1
(45) Date of Patent: Sep. 23, 2003

(54) SYSTEM AND METHOD FOR ELECTROSURGICAL TISSUE CONTRACTION

(75) Inventors: Philip E. Eggers, Dublin, OH (US); Hira V. Thapliyal, Los Altos, CA (US)

(73) Assignee: Arthrocare Corp., Sunnyvale, CA (US)

( * ) Notice: Subject to any disclaimer, the term of this patent is extended or adjusted under 35 U.S.C. 154(b) by 0 days.

(21) Appl. No.: 09/360,075

(22) Filed: Jul. 23, 1999

Related U.S. Application Data

(60) Division of application No. 08/942,580, filed on Oct. 2, 1997, now Pat. No. 6,159,194, which is a continuation-in-part of application No. 08/446,767, filed as application No. PCT/US94/05168 on May 10, 1994, now Pat. No. 5,697,909, which is a continuation-in-part of application No. 08/059,681, filed on May 10, 1993, now abandoned, which is a continuation-in-part of application No. 07/958,977, filed on Oct. 9, 1992, now Pat. No. 5,366,443, which is a continuation-in-part of application No. 07/817,575, filed on Jan. 17, 1992, now abandoned.

(51) Int. Cl.$^7$ ................................................ A61F 7/12
(52) U.S. Cl. ......................................... 604/114; 604/22
(58) Field of Search ............................. 606/39, 41, 46; 607/99, 105, 113; 604/35, 114, 22

(56) References Cited

U.S. PATENT DOCUMENTS

| | | |
|---|---|---|
| 2,050,904 A | 8/1936 | Trice |
| 2,056,377 A | 10/1936 | Wappler |
| 3,815,604 A | 6/1974 | O'Malley et al. |
| 3,828,780 A | 8/1974 | Morrison, Jr. |
| 3,901,242 A | 8/1975 | Storz |
| 3,920,021 A | 11/1975 | Hiltebrandt |
| 3,939,839 A | 2/1976 | Curtiss |
| 3,970,088 A | 7/1976 | Morrison |
| 4,033,351 A | 7/1977 | Hetzel |
| 4,040,426 A * | 8/1977 | Morrison, Jr. |

(List continued on next page.)

FOREIGN PATENT DOCUMENTS

| | | |
|---|---|---|
| DE | 3930451 | 3/1991 |
| EP | 0 703 461 | 3/1996 |
| EP | 0 740 926 A2 | 11/1996 |
| EP | 0 754 437 | 1/1997 |
| FR | 2313949 | 1/1977 |
| GB | 2 308 979 * | 7/1997 |
| GB | 2 308 980 * | 7/1997 |
| GB | 2 308 981 * | 7/1997 |
| GB | 2 327 350 | 1/1999 |
| GB | 2 327 351 | 1/1999 |
| GB | 2 327 352 | 1/1999 |
| JP | 57-57802 | 4/1982 |

(List continued on next page.)

OTHER PUBLICATIONS

Buchelt, M. et al. "Excimer Laser Ablation of Fibrocartilage: An In Vitro and In Vivo Study," (1991) Lasers in Surgery and Medicine 11:271–279.

(List continued on next page.)

*Primary Examiner*—Brian L. Casler
*Assistant Examiner*—Michael M Thompson
(74) *Attorney, Agent, or Firm*—John T. Raffle; Richard R. Batt

(57) ABSTRACT

Systems and methods are provided for performing electrosurgical interventions, such as selectively contracting soft collagen tissue and other body structures, while limiting thermal damage or molecular dissociation of such tissue and limiting the thermal damage to tissue adjacent to and underlying the treatment site. The systems and methods of the present invention are particularly useful for surgical procedures in electrically conducting environments, such as arthroscopic procedures in the joints, e.g., shoulder, knee, hip, hand, foot, elbow or the like. The present invention is also useful in relatively dry environments, such as treating and shaping the cornea, and dermatological procedures involving surface tissue contraction of tissue underlying the surface of the skin for tissue rejuvenation, wrinkle removal and the like.

8 Claims, 21 Drawing Sheets

U.S. PATENT DOCUMENTS

| | | |
|---|---|---|
| 4,043,342 A | 8/1977 | Morrison, Jr. |
| 4,074,718 A | 2/1978 | Morrison, Jr. |
| 4,116,198 A * | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,240,441 A | 12/1980 | Khalil |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A * | 10/1985 | Reimels |
| 4,567,890 A | 2/1986 | Ohta et al. |
| 4,590,934 A | 5/1986 | Malis et al. |
| 4,593,691 A | 6/1986 | Lindstrom et al. |
| 4,660,571 A | 4/1987 | Hess et al. |
| 4,674,499 A | 6/1987 | Pao |
| 4,682,596 A * | 7/1987 | Bales et al. .................... 606/39 |
| 4,706,667 A * | 11/1987 | Roos |
| 4,709,698 A | 12/1987 | Johnston et al. |
| 4,727,874 A | 3/1988 | Bowers et al. |
| 4,765,331 A | 8/1988 | Petruzzi et al. |
| 4,785,823 A | 11/1988 | Eggers et al. |
| 4,805,616 A | 2/1989 | Pao |
| 4,823,791 A * | 4/1989 | D'Amelio et al. |
| 4,832,048 A | 5/1989 | Cohen |
| 4,860,752 A | 8/1989 | Turner |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,955,377 A | 9/1990 | Lennox et al. |
| 4,966,597 A | 10/1990 | Cosman |
| 4,967,765 A | 11/1990 | Turner et al. |
| 4,976,709 A | 12/1990 | Sand |
| 4,976,711 A | 12/1990 | Parins et al. |
| 4,979,948 A | 12/1990 | Geddes et al. |
| 4,998,933 A * | 3/1991 | Eggers et al. .................. 606/41 |
| 5,007,908 A | 4/1991 | Rydell |
| 5,009,656 A | 4/1991 | Reimels |
| 5,035,696 A | 7/1991 | Rydell |
| 5,047,026 A | 9/1991 | Rydell |
| 5,047,027 A | 9/1991 | Rydell |
| 5,057,105 A | 10/1991 | Malone et al. |
| 5,057,106 A | 10/1991 | Kasevich et al. |
| 5,078,717 A | 1/1992 | Parins et al. |
| 5,080,660 A | 1/1992 | Buelna |
| 5,083,565 A | 1/1992 | Parins |
| 5,084,044 A | 1/1992 | Quint |
| 5,085,659 A | 2/1992 | Rydell |
| 5,088,997 A | 2/1992 | Delahuerga et al. |
| 5,092,339 A | 3/1992 | Geddes et al. |
| 5,098,431 A * | 3/1992 | Rydell |
| 5,099,840 A | 3/1992 | Goble |
| 5,108,391 A | 4/1992 | Flachenecker et al. |
| 5,112,330 A | 5/1992 | Nishigaki et al. |
| 5,122,138 A * | 6/1992 | Manwaring .................. 606/46 |
| 5,125,928 A | 6/1992 | Parins et al. |
| 5,137,530 A | 8/1992 | Sand |
| 5,167,659 A | 12/1992 | Ohtomo et al. |
| 5,171,311 A | 12/1992 | Rydell et al. |
| 5,176,528 A | 1/1993 | Fry et al. |
| 5,178,620 A | 1/1993 | Eggers et al. |
| 5,190,517 A | 3/1993 | Zieve et al. |
| 5,192,280 A * | 3/1993 | Parins |
| 5,195,959 A | 3/1993 | Smith |
| 5,197,963 A | 3/1993 | Parins |
| 5,207,675 A | 5/1993 | Canady |
| 5,217,457 A | 6/1993 | Delahuerga et al. |
| 5,217,459 A | 6/1993 | Kamerling |
| 5,230,334 A * | 7/1993 | Klopotek |
| 5,249,585 A | 10/1993 | Turner et al. |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,281,216 A | 1/1994 | Klicek |
| 5,281,218 A | 1/1994 | Imran |
| 5,290,282 A | 3/1994 | Casscells |
| 5,300,069 A | 4/1994 | Hunsberger et al. |
| 5,304,169 A | 4/1994 | Sand |
| 5,306,238 A | 4/1994 | Fleenor |
| 5,312,400 A | 5/1994 | Bales et al. |
| 5,314,406 A | 5/1994 | Arias et al. |
| 5,318,563 A | 6/1994 | Malis et al. |
| 5,324,254 A | 6/1994 | Phillips |
| 5,330,470 A * | 7/1994 | Hagen |
| 5,334,140 A | 8/1994 | Philips |
| 5,334,183 A | 8/1994 | Wuchinich |
| 5,336,220 A | 8/1994 | Ryan et al. |
| 5,342,357 A | 8/1994 | Nardella |
| 5,366,443 A * | 11/1994 | Eggers et al. |
| 5,370,675 A | 12/1994 | Edwards et al. |
| 5,374,265 A * | 12/1994 | Sand |
| 5,380,277 A | 1/1995 | Phillips |
| 5,383,876 A | 1/1995 | Nardella |
| 5,383,917 A | 1/1995 | Desai et al. |
| 5,395,312 A | 3/1995 | Desai |
| 5,417,687 A | 5/1995 | Nardella et al. |
| 5,419,767 A | 5/1995 | Eggers et al. |
| 5,423,810 A | 6/1995 | Goble et al. |
| 5,423,882 A | 6/1995 | Jackman et al. |
| 5,433,708 A | 7/1995 | Nichols et al. |
| 5,436,566 A | 7/1995 | Thompson et al. |
| 5,438,302 A | 8/1995 | Goble |
| 5,441,499 A | 8/1995 | Fritzsch |
| 5,451,224 A | 9/1995 | Goble et al. |
| 5,454,809 A * | 10/1995 | Janssen ...................... 606/41 |
| 5,458,596 A | 10/1995 | Lax et al. |
| 5,496,312 A | 3/1996 | Klicek |
| 5,514,130 A | 5/1996 | Baker |
| 5,556,397 A | 9/1996 | Long et al. |
| 5,569,242 A | 10/1996 | Lax et al. |
| 5,584,872 A | 12/1996 | LaFontaine et al. |
| 5,609,151 A | 3/1997 | Mulier et al. |
| 5,647,869 A * | 7/1997 | Goble et al. |
| 5,660,836 A | 8/1997 | Knowlton |
| 5,662,680 A * | 9/1997 | Desai |
| 5,676,693 A | 10/1997 | LaFontaine et al. |
| 5,681,282 A | 10/1997 | Eggers et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,725,524 A | 3/1998 | Mulier et al. |
| 5,749,869 A | 5/1998 | Lindenmeier et al. |
| 5,766,153 A | 6/1998 | Eggers et al. |
| 5,800,431 A | 9/1998 | Brown |
| 5,807,395 A | 9/1998 | Mulier et al. |
| 5,810,764 A | 9/1998 | Eggers et al. |
| 5,810,809 A | 9/1998 | Rydell |
| 5,843,019 A | 12/1998 | Eggers et al. |
| 5,860,974 A * | 1/1999 | Abele ......................... 606/41 |

| | | |
|---|---|---|
| 5,871,469 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,897,553 A | 4/1999 | Mulier |
| 5,902,272 A | 5/1999 | Eggers et al. |
| 5,944,715 A | 8/1999 | Goble et al. |
| 6,004,319 A | 12/1999 | Goble et al. |
| 6,013,076 A | 1/2000 | Goble et al. |
| 6,015,406 A | 1/2000 | Goble et al. |
| 6,027,501 A | 2/2000 | Goble et al. |
| 6,039,734 A | 3/2000 | Goble et al. |
| 6,056,746 A | 5/2000 | Goble et al. |
| 6,066,134 A | 5/2000 | Eggers et al. |
| 6,068,628 A | 5/2000 | Fanton et al. |
| 6,074,386 A | 6/2000 | Goble et al. |
| 6,090,106 A | 7/2000 | Goble et al. |
| 6,093,186 A | 7/2000 | Goble et al. |
| 6,126,682 A | 10/2000 | Sharkey et al. |
| 6,149,620 A | 11/2000 | Baker et al. |
| 6,159,194 A | 12/2000 | Eggers et al. |
| 6,159,208 A | 12/2000 | Hovda et al. |
| 6,168,593 B1 | 1/2001 | Sharkey et al. |
| 6,179,836 B1 | 1/2001 | Eggers et al. |
| 6,190,381 B1 | 2/2001 | Olsen et al. |
| 6,203,542 B1 | 3/2001 | Ellsberry et al. |
| 6,224,592 B1 | 5/2001 | Eggers et al. |
| 6,228,081 B1 | 5/2001 | Goble |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,264,652 B1 | 7/2001 | Eggers et al. |
| 6,293,942 B1 | 9/2001 | Goble et al. |

FOREIGN PATENT DOCUMENTS

| | | |
|---|---|---|
| | 6,296,636 B1 | 10/2001 Cheng et al. |
| | 6,296,638 B1 | 10/2001 Davison et al. |
| | 6,306,134 B1 | 10/2001 Goble et al. |
| | 6,312,408 B1 | 11/2001 Eggers et al. |
| JP | 57-117843 | 7/1982 |
| WO | 90/03152 | 4/1990 |
| WO | WO 90/07303 | 7/1990 |
| WO | 92/21278 | 12/1992 |
| WO | WO 93/13816 | 7/1993 |
| WO | 93/20747 | 10/1993 |
| WO | WO94/03134 | 2/1994 |
| WO | WO 94/04220 | 3/1994 |
| WO | 94/08654 | 4/1994 |
| WO | WO 94/26228 | 11/1994 |
| WO | WO95/34259 | 12/1995 |
| WO | 96/00042 | 1/1996 |
| WO | WO 96/34568 | 11/1996 |
| WO | WO 97/00646 | 1/1997 |
| WO | WO 97/00647 | 1/1997 |
| WO | WO 97/15238 | 5/1997 |
| WO | 97/24073 | 7/1997 |
| WO | WO 97/24074 | 7/1997 |
| WO | WO 97/24992 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | * 2/1998 |
| WO | 98/27879 | 7/1998 |
| WO | 98/27880 | 7/1998 |
| WO | 99/51155 | 10/1999 |
| WO | 99/51158 | 10/1999 |

OTHER PUBLICATIONS

Costello, A. J. et al. "Nd:YAG Laser Ablation of the Prostate as a Treatment of Benign Prostatic Hypertrophy," (1992) Lasers in Surger and Medicine 12:121–124.

J. W. Ramsey et al. *Urological Research* vol. 13, pp. 99–102 (1985).

R. Tucker et al., Abstract P14–11, p. 248, "A Bipolar Electrosurgical Turp Loop".*

R. Tucker et al. *J. of Urology* vol. 141, pp. 662–665, (1989).*

R. Tucker et al. *Urological Research* vol. 18, pp. 291–294 (1990).*

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

V.E. Elsasser et al. *Acta Medicotechnica* vol. 24, No. 4, pp. 129–134 (1976).

P.C. Nardella (1989) *SPIE* 1068:42–49 Radio Frequency Energy and Impedance Feedback.

Rand et al. (1985) *J. Arthro. Surg.* 1:242–246 Effect of Electrocauteny on Fresh Human Articular Cartilage.

Slager et al. *JACC* 5 (6) :1382–6 (1985).

Pearce, John A. (1986) *Electrosurgery*, pp. 17, 69–75, 87, John Wiley & Sons, New York.

A.K. Dobbie *Bio–Medical Engineering*, vol. 4, pp. 206–216 (1969).

C.P. Swain *Gut* vol. 25, pp. 1424–1431 (1984).

B. Lee et al. *JACC* vol. 13(5), pp. 1167–1175 (1989).

Piercey et al. *Gastroenterology* vol. 74(3), pp. 527–534 (1978).

W. Honig *IEEE* pp. 58–65 (1975).

M.B. Dennis et al. *Digestive Diseases and Sciences* vol. 24(11), pp. 845–848 (1979).

K. Barry et al. *American Heart Journal* vol. 117, pp. 332–341 (1982).

* cited by examiner

SYSTEM AND METHOD FOR ELECTROSURGICAL TISSUE CONTRACTION

CROSS REFERENCES TO RELATED APPLICATIONS

The present invention is a division of U.S. application Ser. No. 08/942,580 filed Oct. 2, 1997, now U.S. Pat. No. 6,159,194, which is a continuation-in-part of U.S. application No. 08/446,767, now U.S. Pat. No. 5,697,909 filed Jun. 2, 1995, which is the national phase of PCT International Application No. PCT/US94/05168, filed on May 10, 1994 which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992 now abandoned, the complete disclosures of which are incorporated herein by reference for all purposes. The present invention is also related to commonly assigned patent applications Ser. No. 08/562,332 filed Nov. 22, 1995 and Ser. No. 08/485,219, filed on Jun. 7, 1995, the complete disclosures of which are incorporated herein by reference for all purposes.

BACKGROUND OF THE INVENTION

The present invention relates generally to the field of electrosurgery and, more particularly, to surgical devices and methods which employ high frequency voltage to contract soft tissue structures, such as collagen connective tissue.

Collagen connective tissue can be found in many places in the human body, such as the soft tissue surrounding joints, the tissue of the cornea, the epidermal and dermal layers of the skin and the like. Collagen fibers shrink or contract when subjected to elevated temperatures, causing the caliber of the collagen fibers to increase without substantially changing the structural integrity of the connective tissue. This molecular response to temperature elevation has made contraction of collagen tissue important in many applications, such as the shrinkage of collagen tissue in the shoulder capsule or knee joint, or the collagen soft tissue in the skin in wrinkle removal procedures.

Collagen tissue is particularly important in the stability of peripheral joints, such as the shoulder, knee, hip, or the like. Peripheral joints generally comprise a covering of hyaline cartilage surrounded by a soft tissue joint capsule that maintains the constant contact of the cartilage surfaces on the ends of bones. This joint capsule also maintains the synovial fluid that provides nutrition and lubrication of the joint surfaces. Instability of peripheral joints is a significant cause of disability and functional limitation in active patients. When a joint becomes unstable, for example, its soft tissue allows for excessive motion of the joint surfaces relative to each other, and in directions not normally permitted by the ligaments or capsule. Typically, the more motion a joint demonstrates, the more inherently loose the soft tissue is surrounding the joint. If the instability is severe and recurrent, functional incapacity and arthritis may result.

Recent surgical attempts to treat joint instability have focused on tightening the soft tissue restraints that have become loose in the joints. These procedures are typically performed through open surgical approaches that often require hospitalization and prolonged rehabilitation programs. Endoscopic techniques generally cause less blood loss, have a lower risk of infection, and faster postoperative recovery times. However, arthroscopic procedures are more technically demanding than open surgical procedures because it is often difficult to access the loose tissue within the joints with endoscopic instruments.

Laser energy has been employed to effect tissue heating for contracting collagen fibers in soft tissue. For example, infrared laser energy has been used on the cornea to induce collagen shrinkage for shape modification of the cornea (laser thermokeratoplasty). In these techniques, the collagen is typically irradiated with laser coherent energy in a wavelength range of about 1.8 to about 2.55 microns to elevate the collagen temperature to about 23° C. above normal body temperature to achieve collagen shrinkage.

Electrosurgery techniques have also been used to contract the collagen fibers in soft tissue. These techniques typically involve the application of radiofrequency (RF) energy to soft collagen tissue to contract and restrict the tissue elasticity. U.S. Pat. No. 5,458,596 to Lax, for example, describes a monopolar electrosurgical device for contracting soft tissue in which RF voltage is applied to an electrode terminal positioned near the target tissue. The electric current is caused to flow through the tissue to induce contraction of the collagen fibers. The transfer of the RF current can be through direct contact between the active electrode and the tissue, or through a thin layer of electrically conducting fluid, such as saline or gel.

Current electrosurgical devices and procedures such as the one described in Lax, however, suffer from a number of disadvantages. For example, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, the direct transfer of RF current through the target tissue tends to increase the thermal damage caused to the target tissue, and it may induce thermal damage or necrosis of body structures underlying and/or surrounding the target tissue.

For these and other reasons, improved systems and methods are desired for the electrosurgical contraction of collagen tissue.

SUMMARY OF THE INVENTION

The present invention provides systems and methods for selectively applying electrical energy to structures within or on the surface of a patient's body. The systems and methods allow the surgical team to perform electrosurgical interventions, such as selectively contracting soft collagen tissue and other body structures, while limiting thermal damage or molecular dissociation of such tissue and limiting the thermal damage to tissue adjacent to and underlying the treatment site. The systems and methods of the present invention are particularly useful for surgical procedures in electrically conducting environments, such as arthroscopic procedures in the joints, e.g., shoulder, knee, hip, hand, foot, elbow or the like. The present invention is also useful in relatively dry environments, such as treating and shaping the cornea, and dermatological procedures involving surface tissue contraction of tissue underlying the surface of the skin for tissue rejuvenation, wrinkle removal and the like.

In one aspect of the present invention, a method for contracting soft collagen tissue involves heating an electrically conducting fluid in the region of the target site, and directing the heated electrically conducting fluid onto the target tissue to induce contraction or shrinkage of the collagen fibers in the target tissue. The electrically conducting fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to an electrode terminal in contact with the electrically conducting fluid. The current emanating from the electrode terminal heats the fluid and generates a jet or plume of heated fluid, which is directed towards the target tissue. The heated fluid elevates the temperature of the collagen sufficiently to cause hydrothermal shrinkage of the collagen fibers.

The electrode terminal may comprise an array of electrode terminals or a single electrode at the distal end of the electrosurgical probe. In a specific embodiment, a return electrode is positioned in contact with the electrically conducting fluid to provide a current flow path from the electrode terminal(s), through the electrically conducting fluid, to the return electrode. The return electrode draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the electrode terminal(s) are held away from the tissue a sufficient distance such that the RF current does not pass into the tissue at all, but rather passes through the electrically conducting fluid back to the return electrode. In this embodiment, the primary mechanism for imparting energy to the tissue is the heated fluid, rather than the electric current.

In another aspect of the invention, the electrode terminal(s) are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration also can be varied with the electrosurgical system of the present invention by changing the frequency of the voltage applied to the electrode terminal and the return electrode. This is because the electrical impedance of tissue is known to decrease with increasing frequency due to the electrical properties of cell membranes which surround electrically conductive cellular fluid. At lower frequencies (e.g., less than 350 kHz), the higher tissue impedance, the presence of the return electrode and the electrode terminal configuration of the present invention (discussed in detail below) cause the current flux lines to penetrate less deeply resulting in a smaller depth of tissue heating. In an exemplary embodiment, an operating frequency of about 100 to 200 kHz is applied to the electrode terminal(s) to obtain shallow depths of collagen shrinkage (e.g., usually less than 1.5 mm and preferably less than 0.5 mm).

In another aspect of the invention, the size (e.g., diameter or principal dimension) of the electrode terminals employed for treating the tissue are selected according to the intended depth of tissue treatment. As described previously in copending patent application PCT International Application, U.S. National Phase Serial No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention and operating at a frequency of about 100 kHz to about 200 kHz. Accordingly, for applications requiring a smaller depth of current penetration, one or more electrode terminals of smaller dimensions would be selected. Conversely, for applications requiring a greater depth of current penetration, one or more electrode terminals of larger dimensions would be selected.

The electrically conducting fluid may be delivered to the target site before or during the surgical procedure. In relatively dry environments, for example, the fluid is delivered along a fluid path past the electrode terminal and the return electrode to the target site to generate the current flow path between the return electrode and the electrode terminal. In other procedures, such as arthroscopic procedures, the electrically conductive fluid is delivered into the arthroscopic cavity to immerse the target site in the fluid. The return electrode is then positioned within the cavity either by introducing the surgical instrument into the cavity or introducing a separate instrument. In an exemplary embodiment, a supplementary lumen is incorporated into the electrosurgical probe to direct a jet of electrically conductive fluid past the electrode(s) to effect a more defined zone of heating on the target tissue surface.

In another aspect of the invention, a method is provided for contracting or shrinking the collagen fibers within a joint capsular tissue, such as the shoulder, knee, hip, hand, foot, elbow or the like, to eliminate capsular redundancy or to otherwise tighten the ligamous complex. In this method, one or more electrode terminal(s) are percutaneously introduced through a portal in the joint and positioned adjacent to the joint capsular tissue. The cavity surrounding the joint is immersed in electrically conducting fluid, such as isotonic saline, and a return electrode is positioned within the electrically conducting fluid. A high frequency voltage difference is applied between the electrode terminal and the return electrode to locally heat the electrically conductive fluid and/or the target tissue adjacent the electrode terminal. In one embodiment, the heated fluid is propelled towards the capsular tissue to induce a contraction of the collagen fibers. In other embodiments, the electrode terminal(s) are brought into contact with, or close proximity to, the capsular tissue to pass RF current directly into the tissue to induce the collagen contraction. In both embodiments, the electric current is drawn proximally towards the return electrode to minimize unnecessary thermal damage to the capsular tissue and to the surrounding and underlying body structures.

In another aspect of the invention, a surgical instrument is provided for applying high frequency energy to tissue at a target site. The instrument includes a shaft and an electrically insulating support at or near the distal end of the shaft. An electrode array of at least three electrode terminals is embedded within the electrically insulating support such that the electrode terminals are substantially flush with the tissue treatment surface of the electrically insulating support. This configuration (i.e., flush electrode terminals) provides a more uniform heating of the fluid, and minimizes high density electric fields that may otherwise form near the edges of electrode terminals. Therefore, sufficient voltage can be applied to the electrode terminals to produce the thermal effects necessary for tissue contraction, while minimizing ablation or dissociation of tissue at or around the target site.

In yet another aspect of the invention, a system is provided for applying high frequency electrical energy to tissue at a target site. The system includes an electrosurgical probe with a shaft and at least one electrode terminal at or near the distal end of the shaft, and a fluid delivery element for delivering electrically conductive fluid to the target site. The system further includes a return electrode spaced from the electrode terminal and an electrosurgical power supply for applying high frequency voltage to the electrode terminal and the return electrode that is sufficient to cause a contraction of collagen fibers within the soft tissue. The return electrode is preferably positioned to induce a substantial portion of the electric current from the electrode terminal away from the tissue at the target site to minimize the depth of current flow into the tissue. The active electrode or electrode terminal is preferably disposed at or near the distal end of the probe and the return electrode is spaced from the active electrode and preferably enclosed within an insulating sheath. This minimizes exposure of the return electrode to surrounding tissue and minimizes possible shorting of the current between the active and return electrodes.

The system may optionally include a temperature controller coupled to one or more temperature sensors at or near the distal end of the probe. The controller adjusts the output voltage of the power supply in response to a temperature set point and the measured temperature value. The temperature sensor may be, for example, a thermocouple, located in the insulating support that measures a temperature at the distal end of the probe. In this embodiment, the temperature set point will preferably be one that corresponds to a tissue temperature that results in the contraction of the collagen tissue, i.e., about 60° C. to 70° C. Alternatively, the temperature sensor may directly measure the tissue temperature (e.g., infrared sensor). This embodiment is advantageous in situations when the surgeon is moving the probe transversely across the tissue.

A further understanding of the nature and advantages of the invention will become apparent by reference to the remaining portions of the specification and drawings.

DESCRIPTION OF SPECIFIC EMBODIMENT

Figure 1:
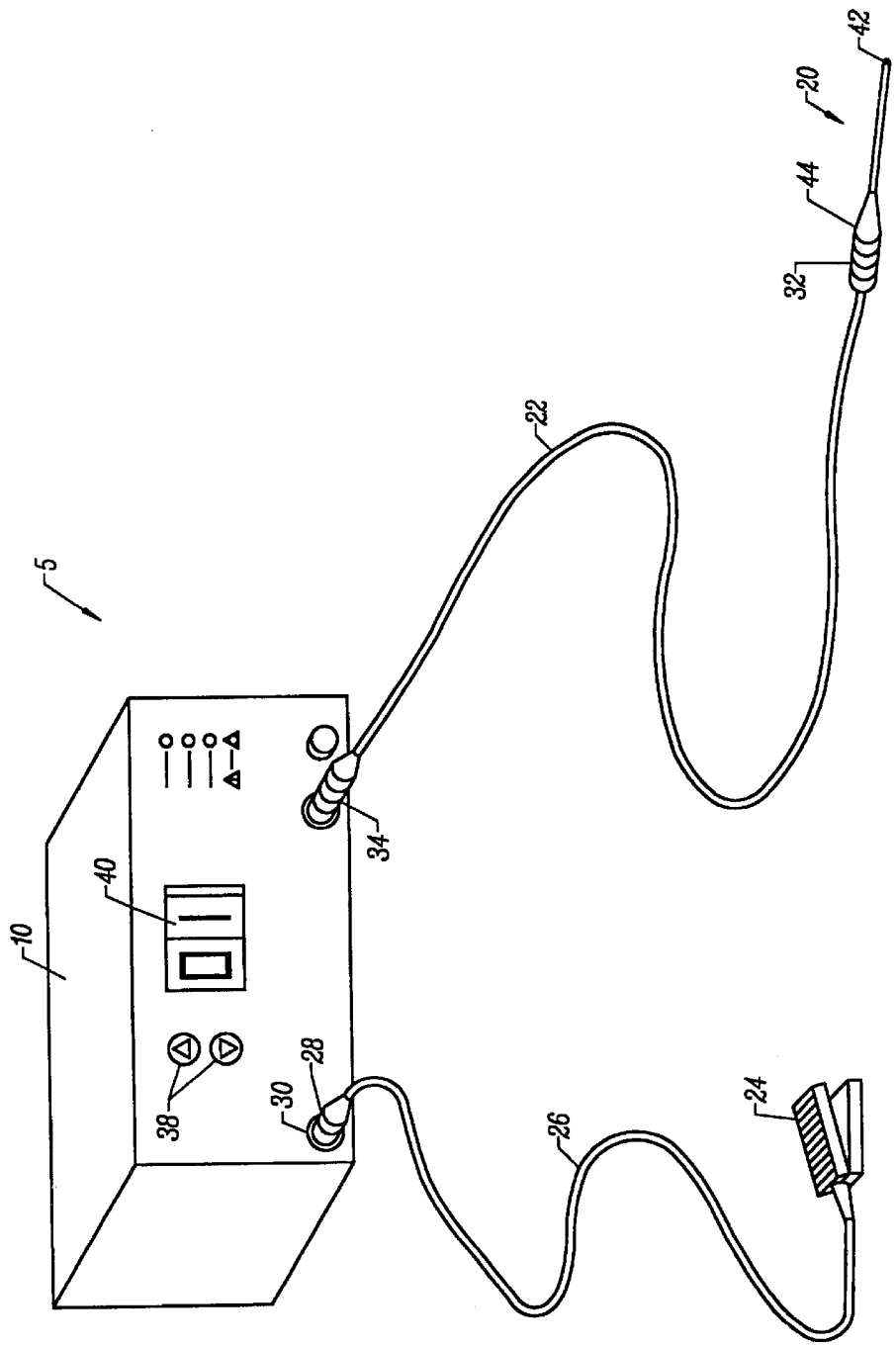
FIG. 1 is a perspective view of an electrosurgical system incorporating a power supply and an electrosurgical probe for tissue contraction and vessel hemostasis according to the present invention.

The present invention provides systems and methods for selectively applying electrical energy to a target location within or on a patient's body, such as solid tissue or the like, particularly including procedures where the tissue site is flooded or submerged with an electrically conducting fluid, such as arthroscopic surgery of the knee, shoulder, ankle, hip, elbow, hand or foot. In addition, tissues which may be treated by the system and method of the present invention include collagenous tissue within the eye or epidermal and dermal tissues underlying the surface of the skin. When applied to a joint, the invention provides shrinkage of the joint capsule and consequent contraction of the volume and interior circumference of the joint capsular to provide joint. stability. For convenience, the remaining disclosure will be directed specifically to the contraction of collagen fibers within a joint during an arthroscopic procedure, but it will be appreciated that the system and method can be applied equally well to procedures involving other tissues of the body, as well as to other procedures including open surgery, laparoscopic surgery, thoracoscopic surgery, and other endoscopic surgical procedures.

The present invention applies high frequency (RF) electrical energy in an electrically conducting fluid environment to shrink or contract collagen connective tissue, such as the collagen capsular tissue within a joint, or the collagen tissue within the epidermal and dermal layers of the skin. The RF energy heats the tissue directly or, indirectly by heating the fluid environment, to elevate the tissue temperature from normal body temperatures (e.g., 37° C.) to temperatures in the range of 55° C. to 85° C., preferably in the range from 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage.

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 0 to 3.5 mm. In the case of joint capsular tissue, the depth of heating is preferably in the range from 0.2 mm to 0.5 mm. In the case of collagen underlying the surface of the skin, the depth of heating is preferably in the range from 0.1 mm to 0.5 mm.

The present invention may use a single active electrode or an electrode array distributed over a contact surface of a probe. The electrode array usually includes a plurality of independently current-limited and/or power-controlled electrode terminals to apply electrical energy selectively to the target tissue and/or the immediate conductive fluid environment, while limiting the unwanted application of electrical energy to the surrounding tissue and environment resulting from power dissipation into surrounding electrically conductive fluids, such as normal saline. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to one or more power sources.

The electrosurgical probe will comprise a shaft having a proximal end and a distal end and one or more electrical connector(s) therebetween for coupling one or more electrode terminal(s) to a high frequency power supply. The shaft may assume a wide variety of configurations, with the primary purpose being to mechanically support the electrode terminal(s) and permit the treating physician to manipulate the electrode terminal(s) from a proximal end of the shaft. Usually, the shaft will be a narrow-diameter rod or tube, more usually having dimensions which permit it to be introduced into a body cavity, such as the mouth or the abdominal cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 0.5 mm and frequently in the range from 1 to 10 mm. Of course, for dermatological procedures on the outer skin, the shaft may have any suitable length and diameter that would facilitate handling by the surgeon.

The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode terminal(s). The shaft will usually include one or more wires or other conductive elements running axially therethrough to permit connection of the electrode terminal(s) to a connector at the proximal end of the shaft. Specific shaft designs will be described in detail in connection with the figures hereinafter.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood or electrically conductive saline irrigant) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum)

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material proximal to the electrode array at the tip which also serves as a conduit for the supply of the electrically conducting fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals, more usually at least four electrode terminals, preferably at least six electrode terminals, and often 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

The voltage applied between the return electrode and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts, and more preferably being in the range from about 20 volts to about 90 volts, and often in the range of about 40 to 70 volts depending on the electrode terminal size and the operating frequency. These frequencies and voltages will result in peak-to-peak voltages and current that are sufficient to heat the electrically conductive fluid to temperatures sufficient to induce contraction of collagen tissue. Typically, the peak-to-peak voltage will be in the range of 10 to 2000 volts and preferably in the range of 20 to 500 volts and more preferably in the range of about 40 to 450 volts (again, depending on the electrode size and the operating frequency).

An important aspect of the present invention is the discovery that the output voltage frequency of the generator can be selected to control the depth of tissue heating. Referring to FIG. 10, the electrical impedance of tissue is known to decrease with increasing frequency due to the electrical properties of cell membranes which surround electrically conductive cellular fluid. As shown, the electrical impedance of tissue to current at a frequency of 100 kHz is on the order of four times larger than at a frequency of 450 to 500 kHz. As a result of the higher tissue impedance, the current flux lines tend to penetrate less deeply resulting in a smaller depth of tissue heating. This principle of operation of the present invention can be used to advantage in applications where the depth of tissue heating is to be maintained small (e.g., 0.2 to 0.5 mm). Preferably, the operating frequency should be below 350 kHz for applications requiring shallow depths of collagen shrinkage (e.g., less than 1.5 mm). Conversely, in situations where much larger depths of collagen shrinkage are to be effected, a higher output voltage frequency may be used. By way of example, to achieve therapeutic collagen shrinkage to a depth of 1.5 to 3.0 mm, a higher operating frequency may be used (e.g., 500 kHz). Alternatively, the diameter of the electrode terminals and/or the spacing between the outer perimeter of the electrode terminals and the electrode support member, $W_3$ (see FIG. 7) may be selected to increase the depth of current penetration. By way of example, increasing the distance $W_3$ will increase the depth of heating, $L_4$ (see FIG. 9) for a given operating frequency.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular arthroscopic surgery, dermatological procedure, ophthalmic procedures, open surgery or other endoscopic surgery procedure.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant), the resistance of the current limiting resistor increases significantly, thereby minimizing the power delivery from said electrode terminal into the low resistance medium (e.g., saline irrigant).

As an alternative to such passive circuit structures, regulated current flow to each electrode terminal may be provided by a multi-channel power supply. A substantially constant current level for each individual electrode terminal within a range which will limit power delivery through a low resistance path, e.g., isotonic saline irrigant, and would be selected by the user to achieve the desired rate of tissue heating. Such a multi-channel power supply thus provides a substantially constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrode terminals to be simultaneously energized and which include active control means for limiting current levels below a preselected maximum level. In this arrangement, only one or several electrode terminals would be simultaneously energized for a brief period. Switching means would allow the next one or several electrode terminals to be energized for a brief period. By sequentially energizing one or several electrode terminals, the interaction between adjacent electrode terminals can be minimized (for the case of energizing several electrode terminals positioned at the maximum possible spacing within the overall envelope of the electrode array) or eliminated (for the case of energizing only a single electrode at any one time). As before, a resistance measurement means may be employed for each electrode terminal prior to the application of power wherein a (measured) low resistance (below some preselected level) will prevent that electrode terminal from being energized during a given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrode terminals. In addition, the present invention includes the means to measure the resistance of the medium in contact with each electrode terminal and cause voltage to be applied only if the resistance exceeds a preselected level. A more complete description of suitable mechanisms for limiting current to individual electrode terminals can be found in PCT International Application, U.S. National Phase Serial No. PCT/US94/05168, filed on May 10, 1994 (Attorney Docket 16238-000440), the complete disclosure of which has previously been incorporated herein by reference.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

The electrode terminal(s) are formed over a tissue treatment surface on the shaft of the electrosurgical probe. The return electrode surface will be recessed relative to the distal end of the probe and may be recessed within a fluid conduit provided for the introduction of electrically conducting fluid to the site of the target tissue and electrode terminal(s). In the exemplary embodiment, the shaft will be cylindrical over most of its length, with the tissue treatment surface being formed at the distal end of the shaft. In the case of endoscopic applications, the tissue treatment surface may be recessed since it helps to protect and shield the electrode terminals on the surface while they are being introduced, particularly while being introduced through the working channel of a trocar channel or a viewing scope.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

Referring now to FIG. 1, an exemplary electrosurgical system 5 for contraction of collagen tissue will now be described in detail. As shown, electrosurgical system 5 generally includes an electrosurgical probe 20 connected to a power supply 10 for providing high frequency voltage to one or more electrode terminals (not shown in FIG. 1) on probe 20. Probe 20 includes a connector housing 44 at its proximal end, which can be removably connected to a probe receptacle 32 of a probe cable 22. The proximal portion of cable 22 has a connector 34 to couple probe 20 to power supply 10. Power supply 10 has an operator controllable voltage level adjustment 38 to change the applied voltage level, which is observable at a voltage level display 40. Power supply 10 also includes a foot pedal 24 and a cable 26 which is removably coupled to a receptacle with a cable connector 28. The foot pedal 24 may also include a second pedal (not shown) for remotely adjusting the energy level applied to electrode terminals 104. The specific design of a power supply which may be used with the electrosurgical probe of the present invention is described in parent application PCT US 94/051168, the full disclosure of which has previously been incorporated herein by reference.

Figure 2:
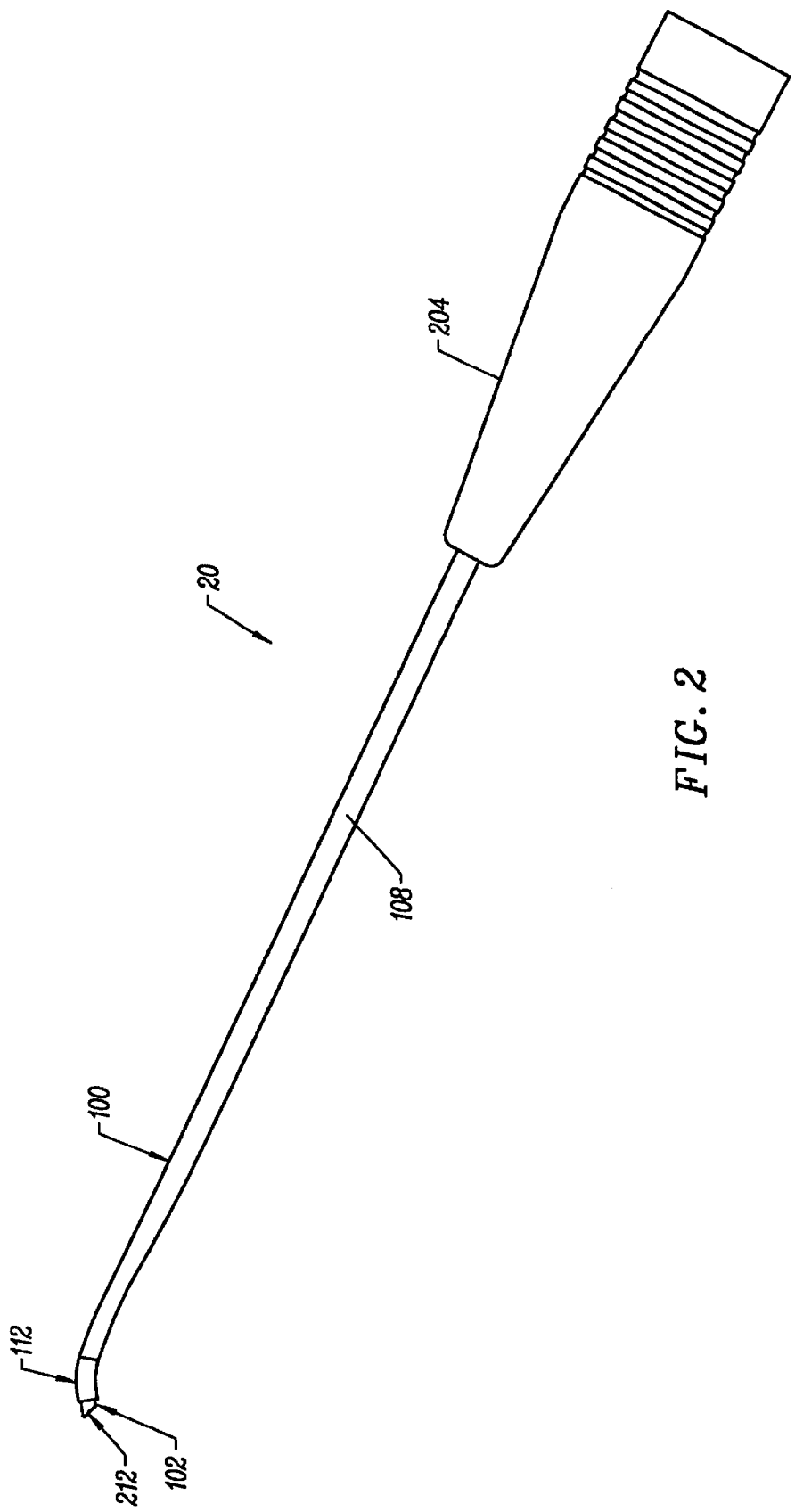
FIG. 2 is a side view of the electrosurgical probe of FIG. 1.

FIGS. 2–5 illustrate an exemplary electrosurgical probe 20 constructed according to the principles of the present invention. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group consisting of tungsten, stainless steel alloys, platinum or its alloys, titanium or its alloys, molybdenum or its alloys, and nickel or its alloys. Shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Figure 3:
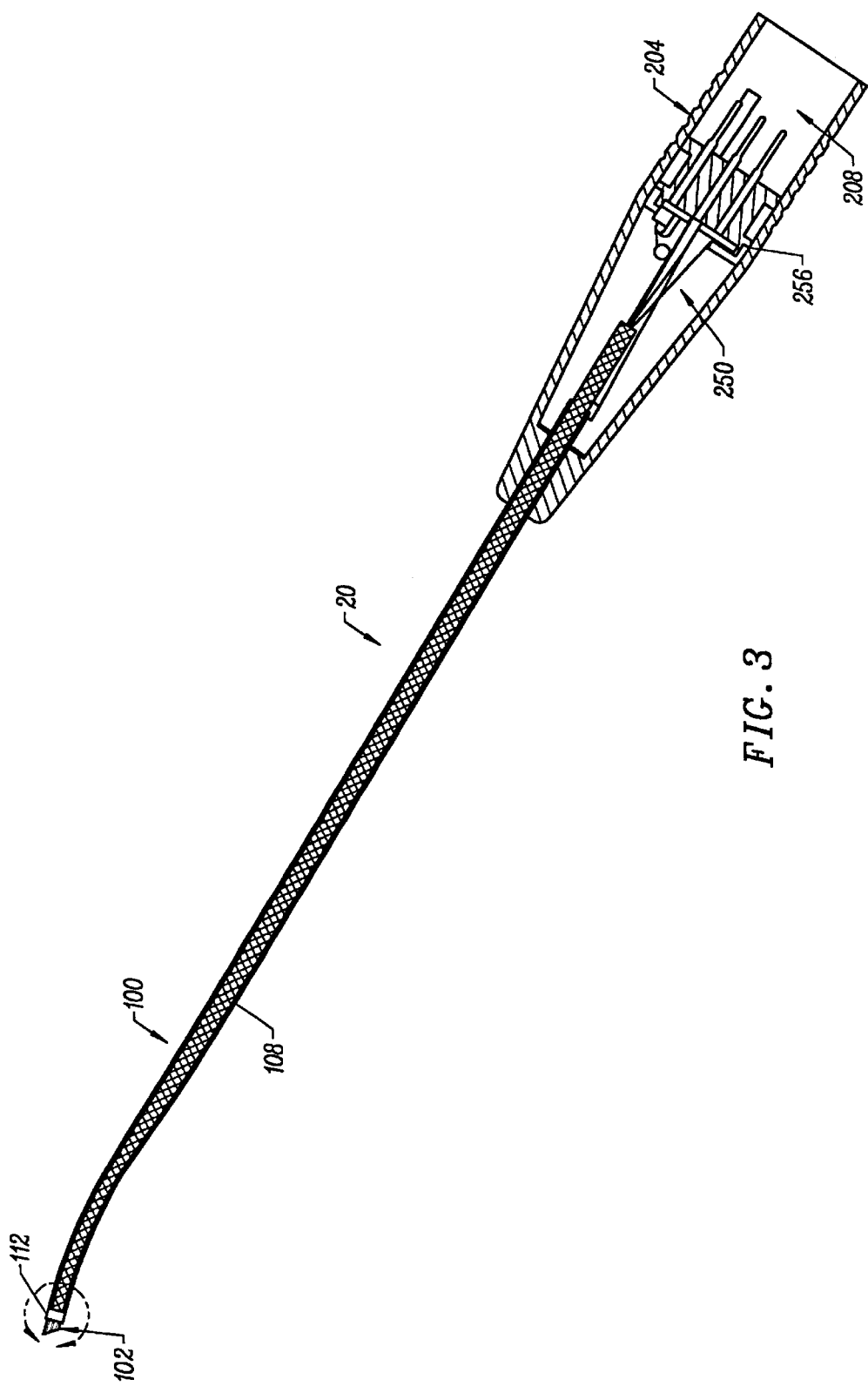
FIG. 3 is a cross sectional view of the electrosurgical probe of FIG. 1.

Handle 204 typically comprises a plastic material that is easily molded into a suitable shape for handling by the surgeon. As shown in FIG. 3, handle 204 defines an inner cavity 208 that houses the electrical connections 250 (discussed below), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIG. 5).

As shown in FIG. 2, the distal portion of shaft 100 is preferably bent to improve access to the operative site of the tissue being treated (e.g., contracted). Electrode support member 102 has a substantially planar tissue treatment surface 212 that is usually at an angle of about 10 to 90 degrees relative to the longitudinal axis of shaft 100, preferably about 30 to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT International Application, U.S. National Phase Serial No. PCT/US94/05168, filed on May 10, 1994 (Attorney Docket 16238-000440), the complete disclosure of which has previously been incorporated herein by reference.

The bend in the distal portion of shaft 100 is particularly advantageous in arthroscopic treatment of joint capsular tissue as it allows the surgeon to reach the target tissue within the joint as the shaft 100 extends through a cannula or portal. Of course, it will be recognized that the shaft may have different angles depending on the procedure. For example, a shaft having a 90° bend angle may be particularly useful for accessing tissue located in the back portion of a joint compartment and a shaft having a 10° to 30° bend angle may be useful for accessing gingiva near or in the front portion of the joint compartment.

Figure 5:
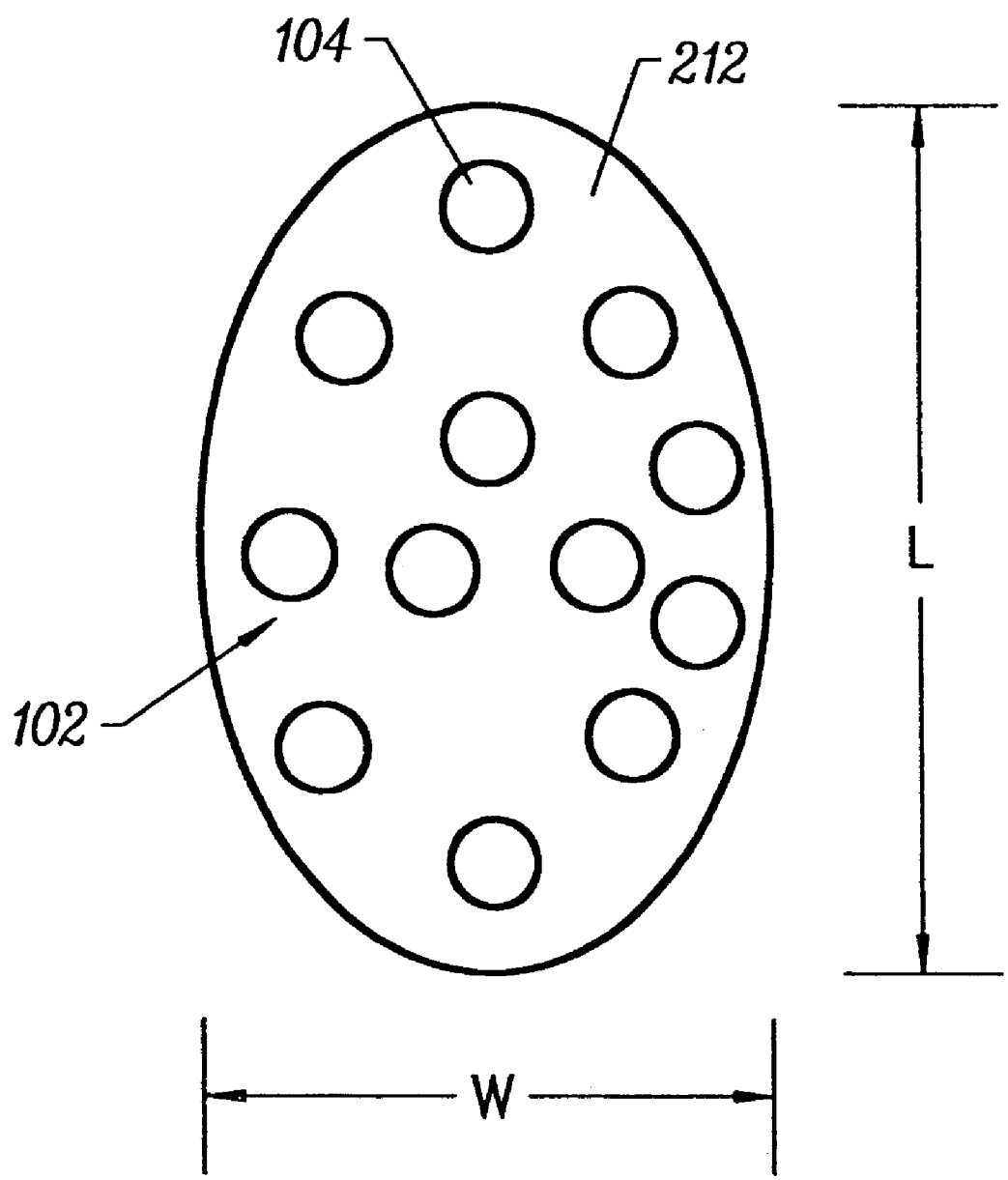
FIG. 5 is an end view of the probe illustrating an array of electrode terminals embedded within a support.

Referring to FIG. 5, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has an oval cross-sectional shape with a length L in the range of 1 mm to 20 mm and a width W in the range from 0.3 mm to 7 mm. The oval cross-sectional shape accommodates the bend in the distal portion of shaft 202. The individual electrode terminals 104 are preferably substantially flush with tissue treatment surface 212. Applicant has found that this configuration minimizes any sharp electrode edges and/or corners that would promote excessively high electric field intensities and associated current densities when a high frequency voltage is applied to the electrode terminals.

It should be noted that the electrode terminals 104 may protrude slightly outward from surface 212, typically by a distance from 0 mm to 2 mm, or the terminals may be recessed from this surface. For example, the electrode terminals 104 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

In the embodiment shown in FIGS. 2–5, probe 20 includes a return electrode 112 for completing the current path between electrode terminals 104 and a high frequency power supply 10 (see FIG. 1). As shown, return electrode 112 preferably comprises an annular exposed region of shaft 102 slightly proximal to tissue treatment surface 212 of electrode support member 102, typically about 0.5 to 10 mm and more preferably about 1 to 10 mm. Return electrode 112 is coupled to a connector 258 that extends to the proximal end of probe 10, where it is suitably connected to power supply 10 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered from a fluid delivery element (not shown) that is separate from probe 20. In arthroscopic surgery, for example, the body cavity will be flooded with isotonic saline and the probe 20 will be introduced into this flooded cavity. Electrically conducting fluid will be continually resupplied to maintain the conduction path between return electrode 112 and electrode terminals 104.

In alternative embodiments, the fluid path may be formed in probe 20 by, for example, an inner lumen or an annular gap (not shown) between the return electrode and a tubular support member within shaft 100. This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in commonly assigned, co-pending application Ser. No. 08/485,219, filed on Jun. 7, 1995 (Attorney Docket 16238-0006000), the complete disclosure of which has previously been incorporated herein by reference.

Figure 4:
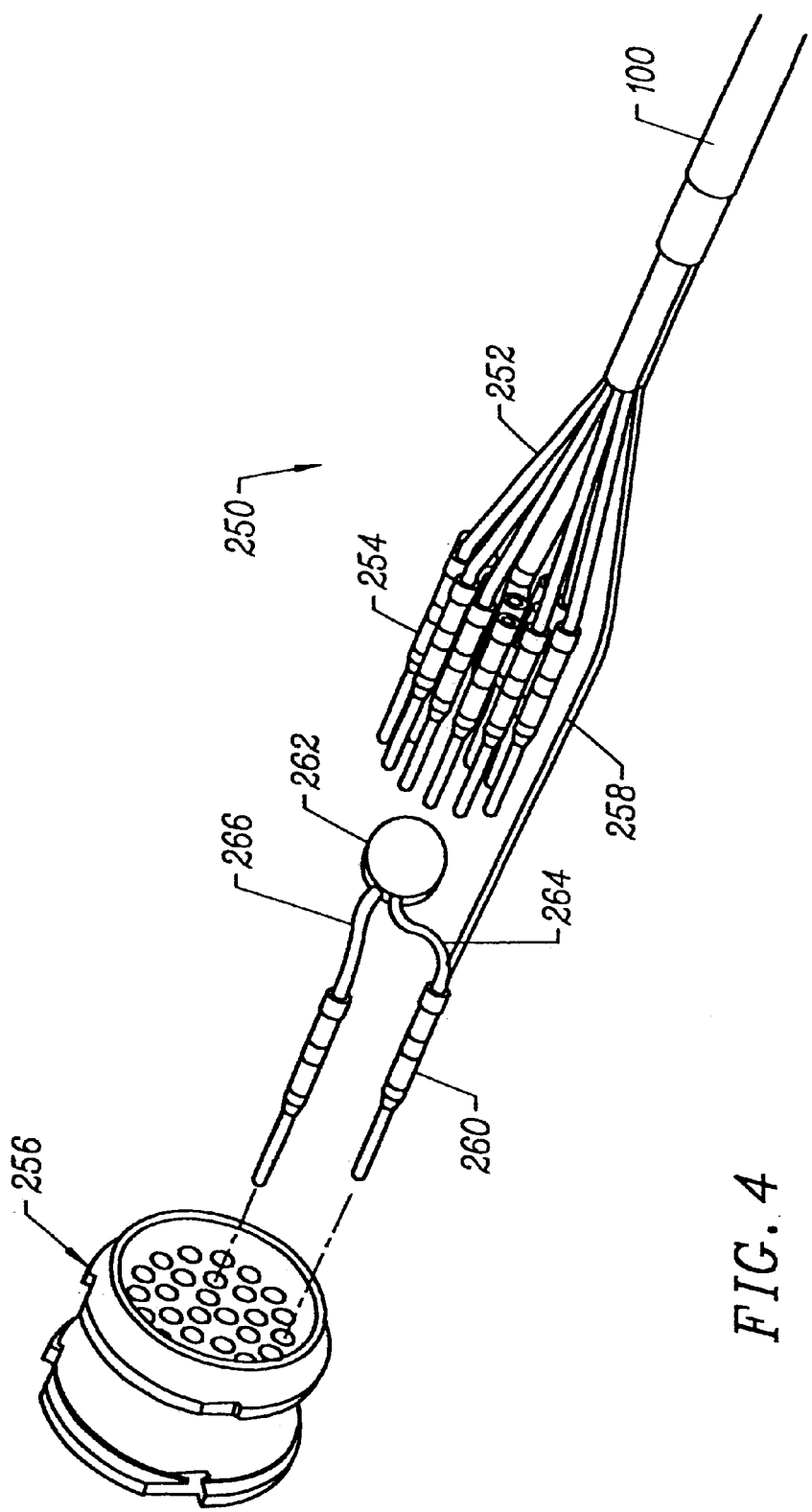
FIG. 4 is an exploded view of a proximal portion of the electrosurgical probe.

FIG. 4 illustrates the electrical connections 250 within handle 204 for coupling electrode terminals 104 and return electrode 112 to the power supply 10. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, the probe 20 further includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe to be compatible with other ArthroCare generators that are adapted to apply higher voltages for ablation or vaporization of tissue. Usually, the voltage reduction element will serve to reduce a voltage of about 100 to 135 volts rms (which is a setting of 1 on the ArthroCare Model 970 and 980 (i.e., 2000) Generators) to about 45 to 60 volts rms, which is a suitable voltage for contraction of tissue without ablation (i.eg., molecular dissociation) of the tissue.

In the representative embodiment, the voltage reduction element is a dropping capacitor 262 which has first leg 264 coupled to the return electrode wire 258 and a second leg 266 coupled to connector block 256. The capacitor usually has a capacitance of about 2700 to 4000 pF and preferably about 2900 to 3200 pF. Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 20 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 20 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

Further, it should be noted that the present invention can be used with a power supply that is adapted to apply a voltage within the selected range for contraction of tissue. In this embodiment, a voltage reduction element or circuitry would not be desired.

Figure 6:
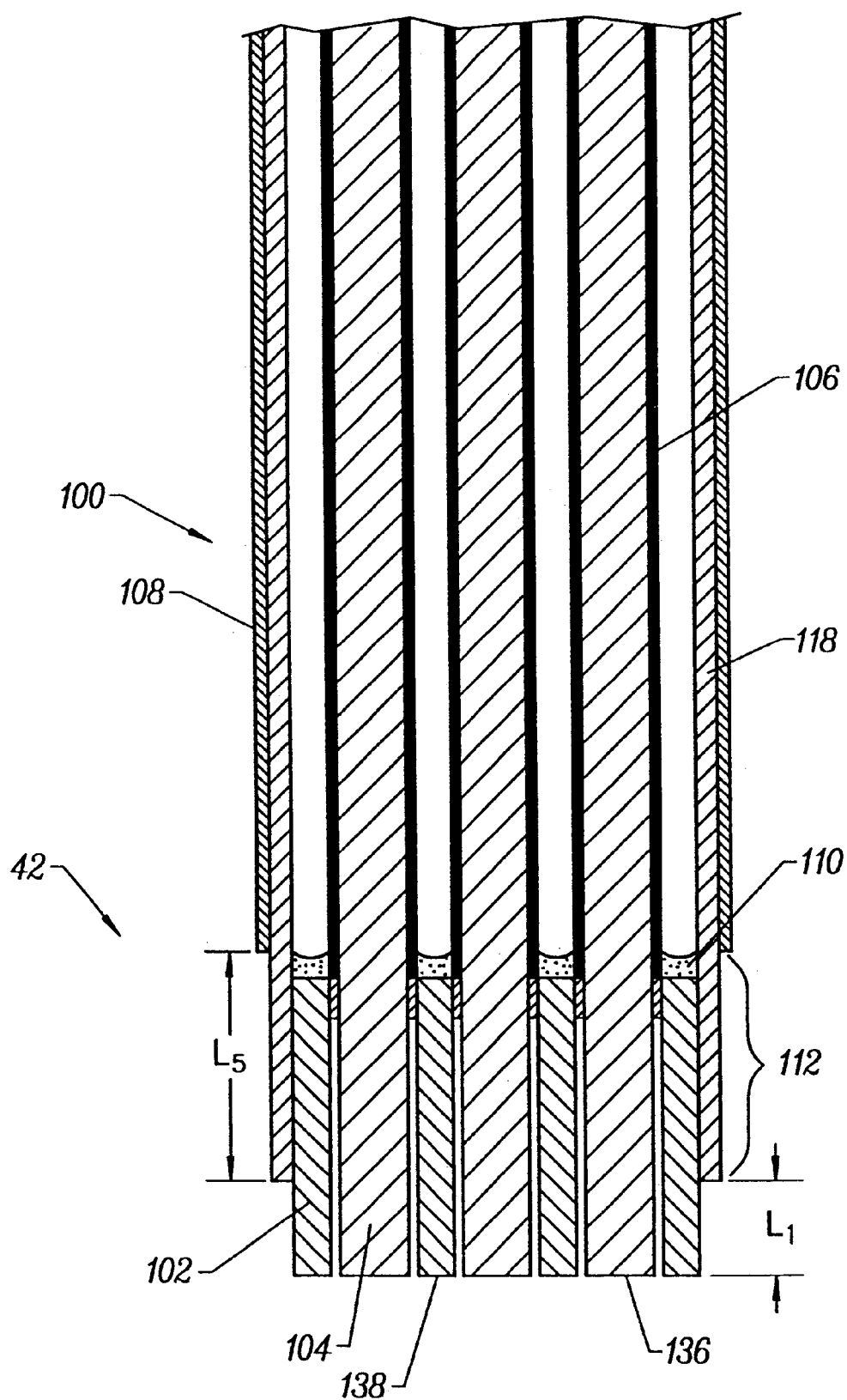
FIG. 6 is a sectional view of the distal portion of an electrosurgical probe according to the present invention.
Figure 7:
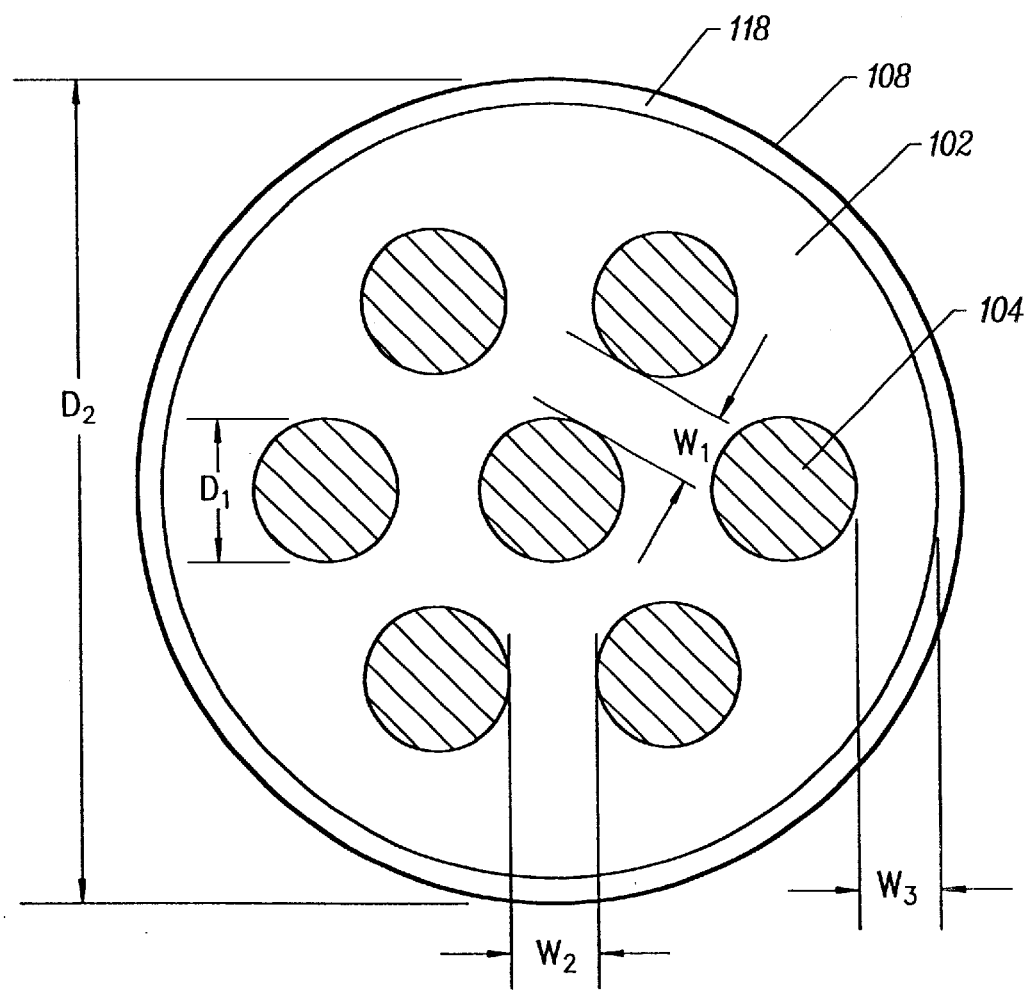
FIG. 7 is an end view of the probe of FIG. 5.

Referring to FIGS. 6 and 7, one embodiment of the distal or working end 42 of electrosurgical probe 200 will now be described. As shown, the probe includes a shaft 100 with two or more electrode terminals 104 whose distal ends are secured in an electrode support member 102. Electrode support member 102 may be secured to cannula 118 by adhesive 110. As shown in FIG. 7, the distal surfaces 136 of active electrodes 104 are in the same plane as the distal surface 138 of electrode support member 102. Applicant has found that this configuration minimizes any sharp electrode edges and/or corners that would promote high electric field intensities and associated current densities when a high frequency voltage is applied to the electrode terminals. The surfaces of electrode terminals 104 proximal to electrode support member 102 are covered with electrically insulating layer 106. Each electrode terminal 104 is secured in electrode support member 102 using adhesive 110. The cannula 118 is covered with electrically insulating sleeve 108 except over length, $L_5$ at the distal end of cannula 118. The exposed length, $L_5$ of cannula 128 serves as return electrode 112 to provide an electrical pathway between the electrode terminals 104 and return electrode 112.

The electrode terminals 104 may be constructed using round, square, rectangular or other shaped conductive metals. By way of example, the electrode terminal materials may be selected from the group including stainless steel, tungsten and its alloys, molybdenum and its alloys, titanium and its alloys, nickel-based alloys, as well as platinum and its alloys. Electrode support member 102 is preferably a ceramic glass or glass/ceramic composition (e.g., aluminum oxide, titanium nitride). Alternatively, electrode support member 102 may include the use of high-temperature biocompatible plastics such as polyether-ether-keytone (PEEK) manufactured by Vitrex International Products, Inc. or polysulfone manufactured by GE Plastics. The adhesive 110 may, by way of example, be an epoxy (e.g., Master Bond EP42HT) or a silicone-based adhesive. The cannula 118 may be selected from the group including stainless steel, copper-based alloys, titanium or its alloys, and nickel-based alloys.

Electrically insulating sleeve 108 may be a coating (e.g., nylon) or heat shrinkable plastic (e.g., fluropolymer or polyester). The electrically insulating layer 106 may be a polyimide or Teflon coating or may be a polyethylene covering.

In the first embodiment and referring to FIG. 7, a total of 7 circular active electrodes or electrode terminals 104 are shown in a symmetrical pattern having an active electrode diameter, $D_1$ in the range from 0.05 mm to 1.5 mm, more preferably in the range from 0.1 mm to 0.75 mm. The interelectrode spacings, $W_1$ and $W_2$ are preferably in the range from 0.1 mm to 1.5 mm and more preferably in the range from 0.2 mm to 0.75 mm. The distance between the outer perimeter of the electrode terminal 104 and the perimeter of the electrode support member, $W_3$ is preferably in the range from 0.1 mm to 1.5 mm and more preferably in the range from 0.2 mm to 0.75 mm. The overall diameter, $D_2$ of the working end 42 of probe 20 is preferably in the range from 0.5 mm to 10 mm and more preferably in the range from 1.0 mm to 5 mm. As discussed above, the shape of the active electrodes may be round (as shown in FIG. 7), square, triangular, hexagonal, rectangular, tubular, flat strip and the like and may be arranged in a circularly symmetric pattern as shown in FIG. 7 or may, by way of example, be arranged in a rectangular pattern, square pattern, or strip pattern as shown in FIGS. 8A through 8D.

Referring to FIGS. 6 and 7, the thickness of the cannula 118 is preferably in the range from 0.08 mm to 1.0 mm and more preferably in the range from 0.1 mm to 0.4 mm. As stated previously, the material for the cannula 118 may be advantageously selected from a group of electrically conductive metals so that the cannula functions as both a structural support member for the array of electrode terminals 104 as well as a return electrode 112. The cannula 118 is connected to an electrical lead wire at its proximal end within connector housing 44 (not shown) and continues via probe cable 22 to generator 10 to provide electrical continuity between one output pole of high frequency generator 10 and said return electrode 112. The thickness of the electrically insulating sleeve 108 is preferably in the range from 0.01 mm to 0.5 mm and more preferably in the range from 0.02 mm to 0.2 mm. The thickness of the electrically insulating layer 106 on the proximal portions of the electrode terminals 104 is preferably in the range from 0.01 mm to 0.5 mm and more preferably in the range from 0.02 mm to 0.2 mm.

Referring now to FIG. 6, the length of the return electrode, $L_5$ is preferably in the range from 1 mm to 30 mm and more preferably in the range from 2 mm to 20 mm. The spacing between the most distal portion of the return electrode 112 and the plane of the distal surface 138 of the electrode support member, $L_1$ is preferably in the range from 0.5 mm to 30 mm and more preferably in the range from 1 mm to 20 mm.

Figure 8B:
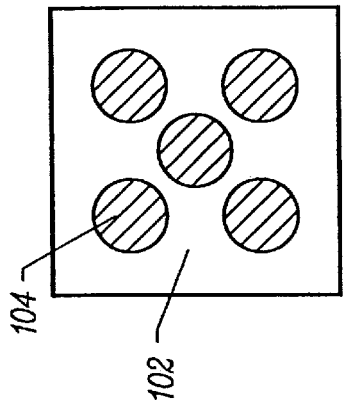
FIGS. 8A–8D are end views of alternative configurations for the probe of FIG. 6.
Figure 8D:
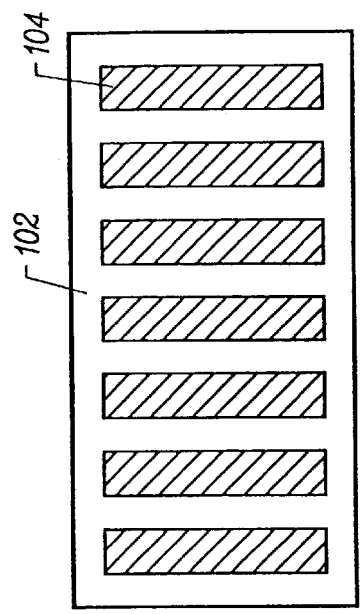
Figure 8A:
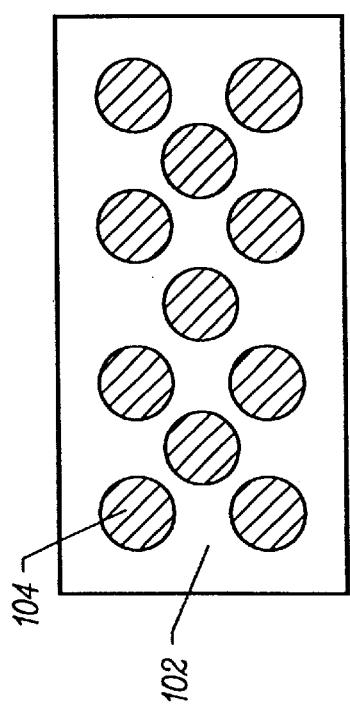
Figure 8C:
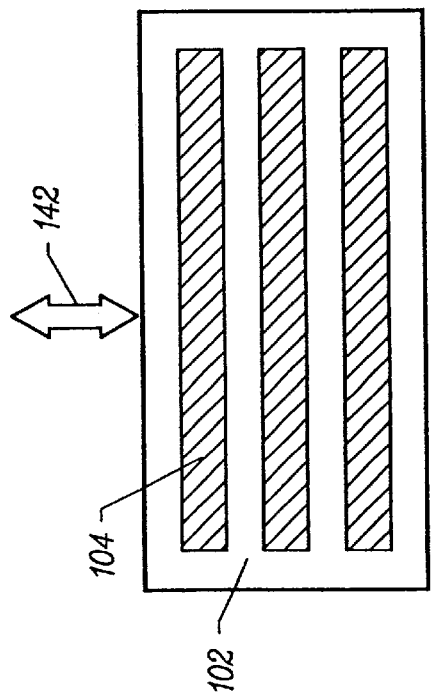

FIGS. 8A–8D illustrate alternative embodiments of the end of the electrosurgical probe. As shown, the distal surface 102 of the probe may have a substantially square or rectangular shape. FIGS. 8C and 8D illustrate embodiments with linear or band shaped electrodes 104. Typically, the probe is moved laterally in the direction of arrows 142 perpendicular to the longitudinal axis of the linear electrodes 104. This embodiment provides a substantially uniform application of thermal energy over a relative larger area, and is particularly advantageous in treatment of external body surfaces, such as wrinkle removal procedures.

Figure 9:
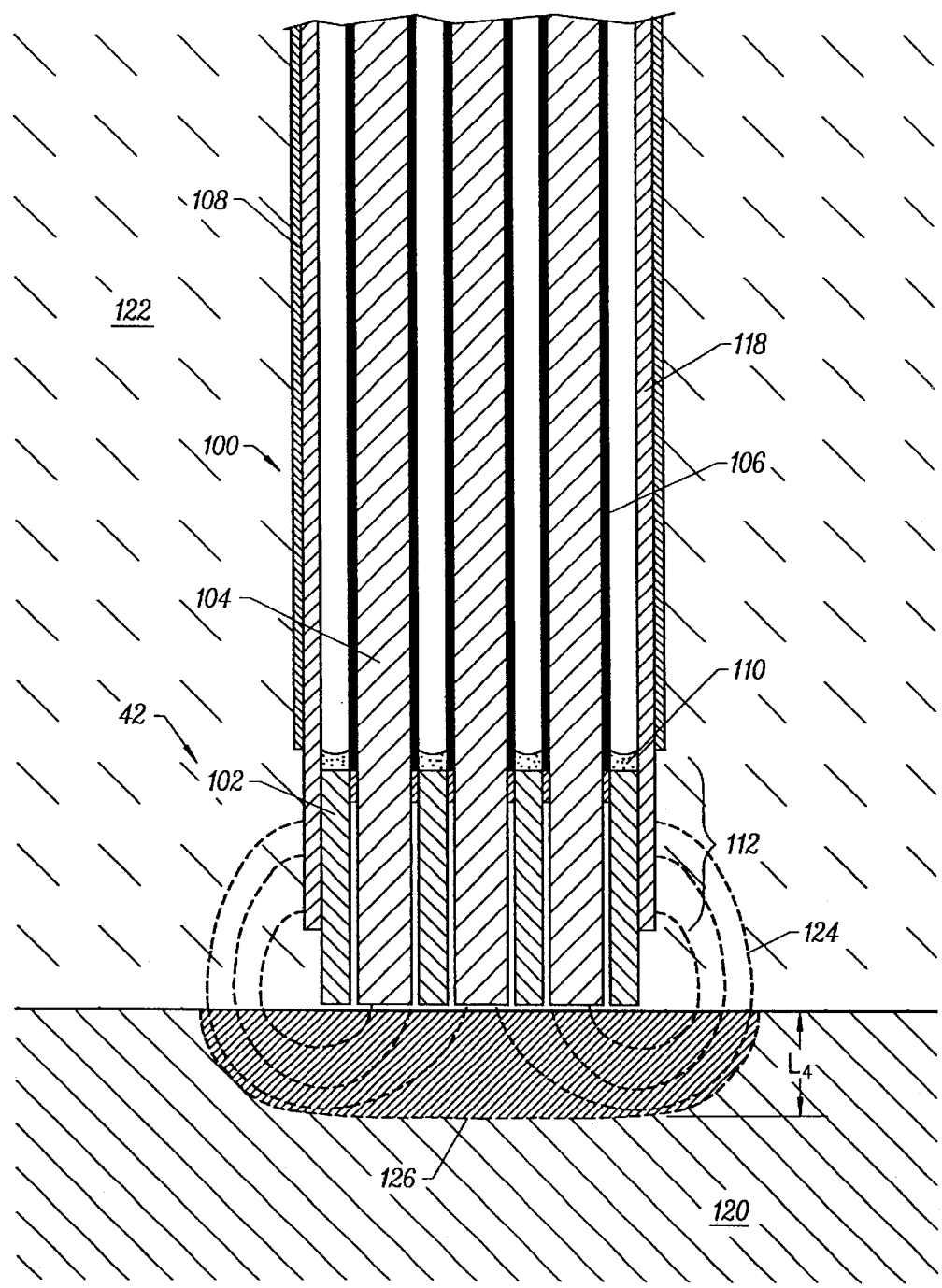
FIG. 9 is a view of the distal portion of the electrosurgical probe of FIG. 6, illustrating use of the probe for contraction of collagen fibers in an electrically conducting environment.
Figure 10:
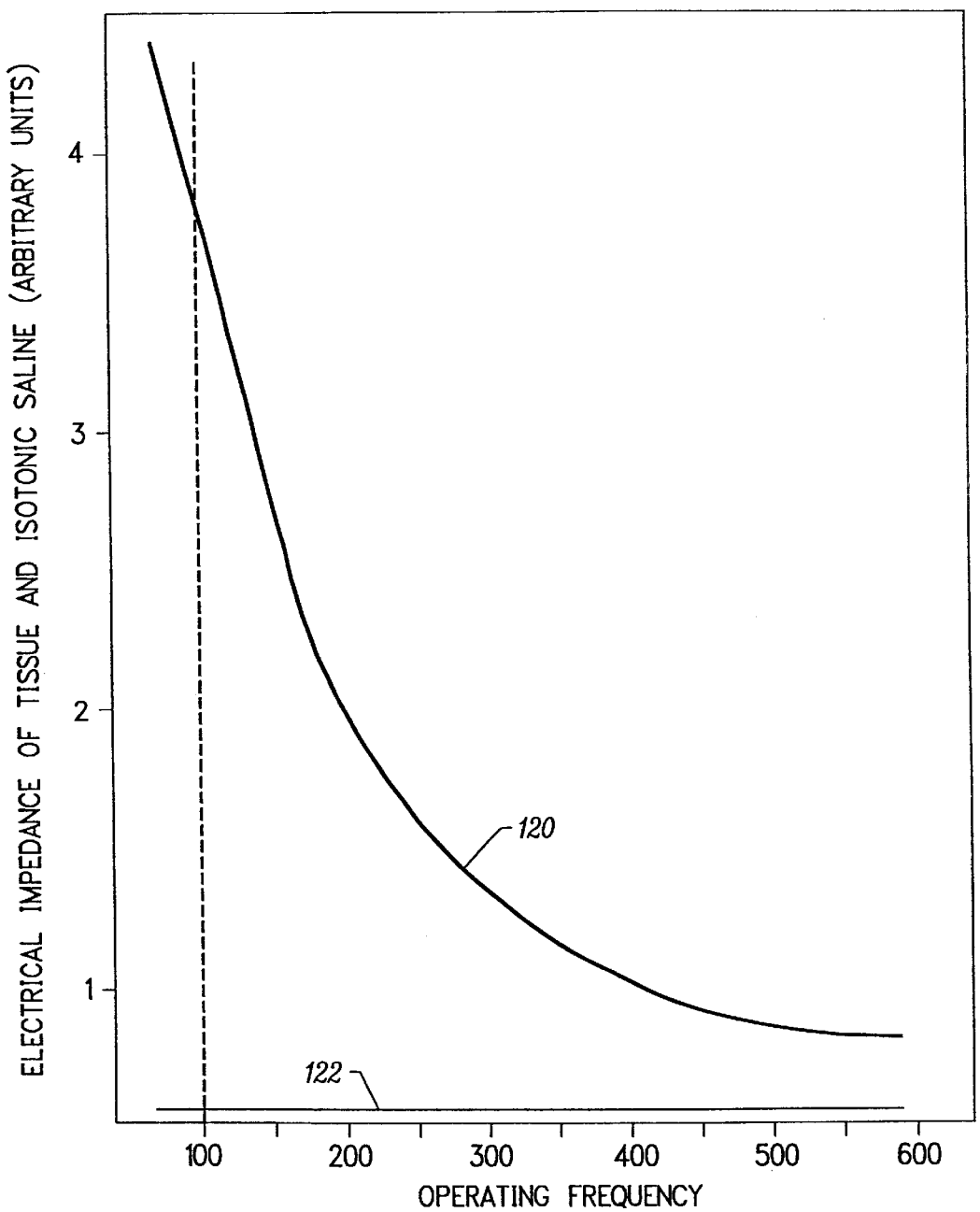
FIG. 10 is a graph illustrating the electrical impedance of tissue and isotonic saline with operating frequency.
Figure 11:
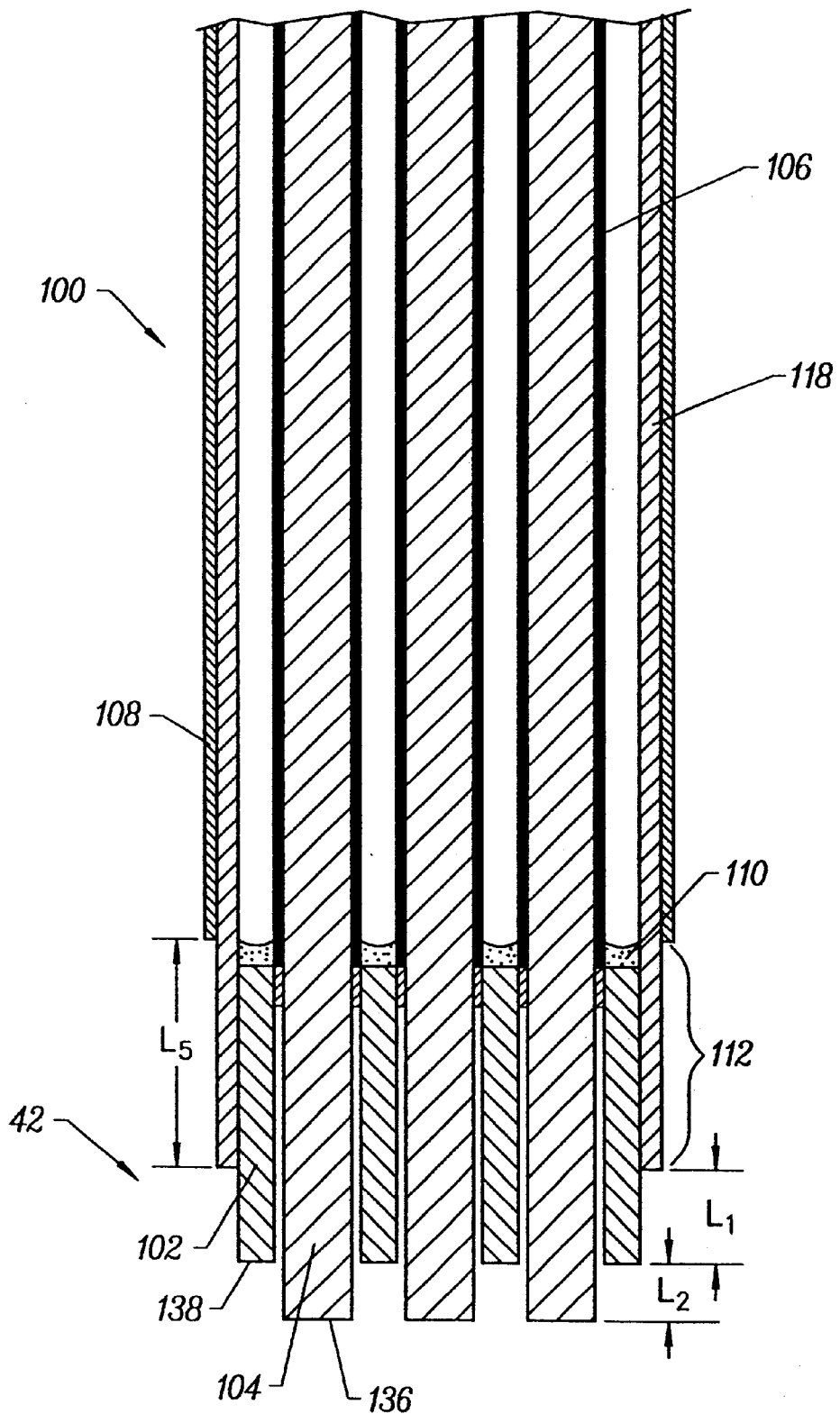
FIGS. 11 and 12 are sectional views illustrating another electrosurgical probe and method for contraction of collagen tissue according to the present invention.
Figure 12:
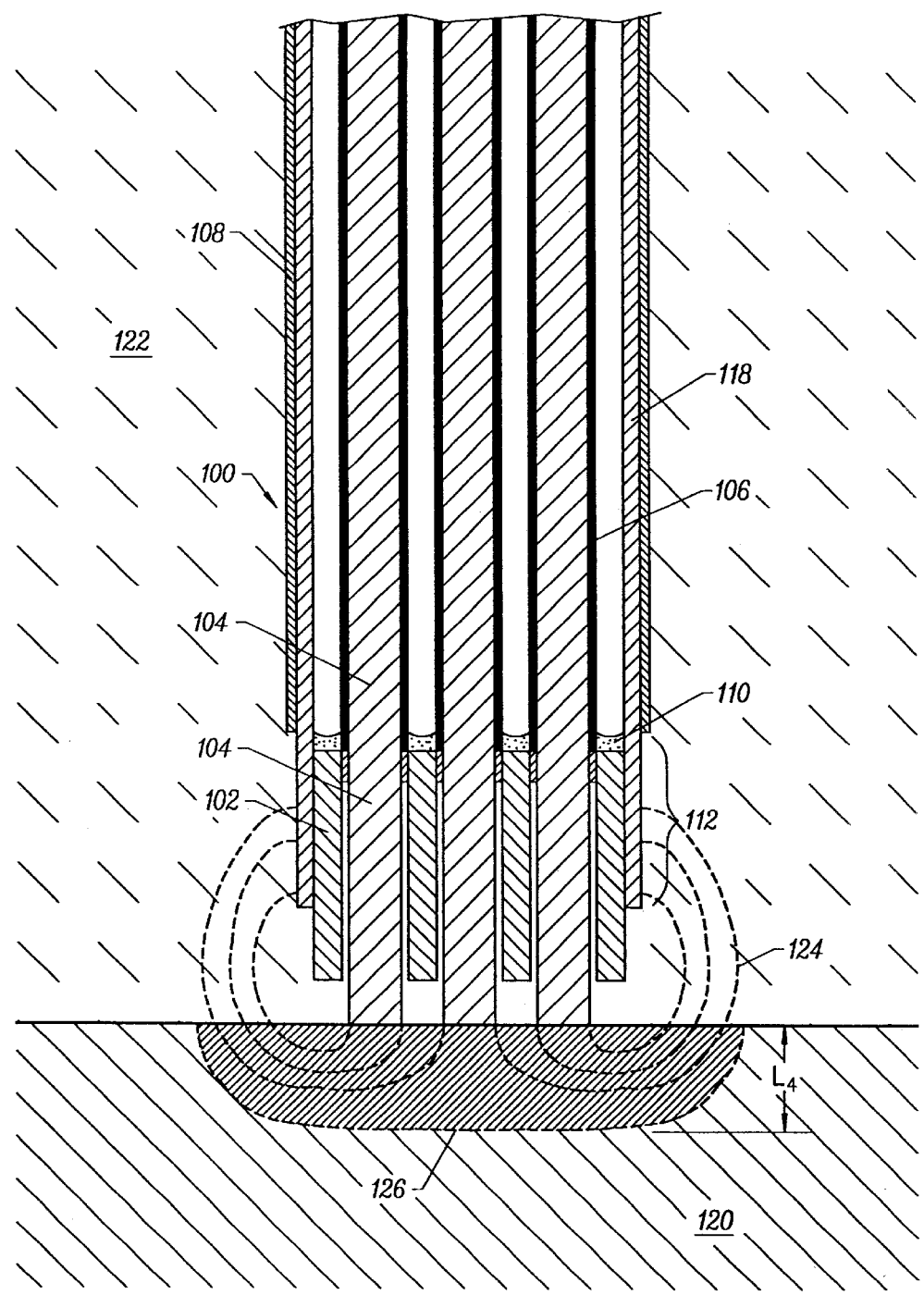

Referring now to FIG. 9, the working end 42 of probe 20 is shown in contact with or in close proximity to a target tissue 120. In particular, electrode terminals 104 are in contact or in close proximity with tissue 120. The volume which surrounds the working end 42 of probe 20 is filled with an electrically conductive fluid 122 which may, by way of example, be isotonic saline or other biocompatible, electrically conductive irrigant solution. When a voltage is applied between the electrode terminals 104 and the return electrode 112, electrical current flows between the electrode terminals 104 and the return electrode 112 along current flux lines 124. The current flux lines 124 flow a short distance, $L_4$, into the surface of tissue 120 and through the electrically conductive fluid 122 in the region above the surface of the tissue to complete the electrical path between the electrode terminals 124 and the return electrode 112. As a consequence of the electrical impedance of the tissue and the proper selection of the applied voltage and current, heating of the tissue 120 occurs in a region 126 (shaded) below the surface of the tissue 120, Another embodiment of the present invention is illustrated in FIG. 11 and 12. This embodiment is similar previous embodiments except that distal surface 136 of the electrode terminals 104 extends beyond the plane of the distal surface 138 of the electrode support member 102 by an extension length, $L_1$. This extension length, $L_2$, is preferably in the range from 0.05 mm to 2 mm and more preferably is in the range from 0.1 mm to 0.5 mm. All other dimensions and materials of construction are similar to those defined for the first embodiment described above. As shown in FIG. 12, the distal surfaces 136 of the electrode terminals 104 are in close proximity with or in direct contact with the surface of tissue 120.

The volume which surrounds the working end of probe 20 is filled with an electrically conductive fluid 122 which may, by way of example, be isotonic saline or other biocompatible, electrically conductive irrigant solution. When a voltage difference is applied between the electrode terminals 104 and the return electrode 112, electrical current flows between the electrode terminals 104 and the return electrode 112 along current flux lines 124. The current flux lines 124 flow a short distance, $L_4$ into the surface of tissue 120 and through the electrically conductive fluid 122 in the region above the surface of the tissue to complete the electrical path between the electrode terminals 104 and the return electrode 112. As a consequence of the electrical impedance of the tissue and the proper selection of the applied voltage and current, heating of the tissue 120 occurs in a region 126 below the surface of the tissue 120, said heating elevating the temperature of the tissue from normal body temperature (e.g. 37° C.) to a temperature in the range 55° C. to 85° C., preferably in the range from 60° C. to 70° C.

Figure 13:
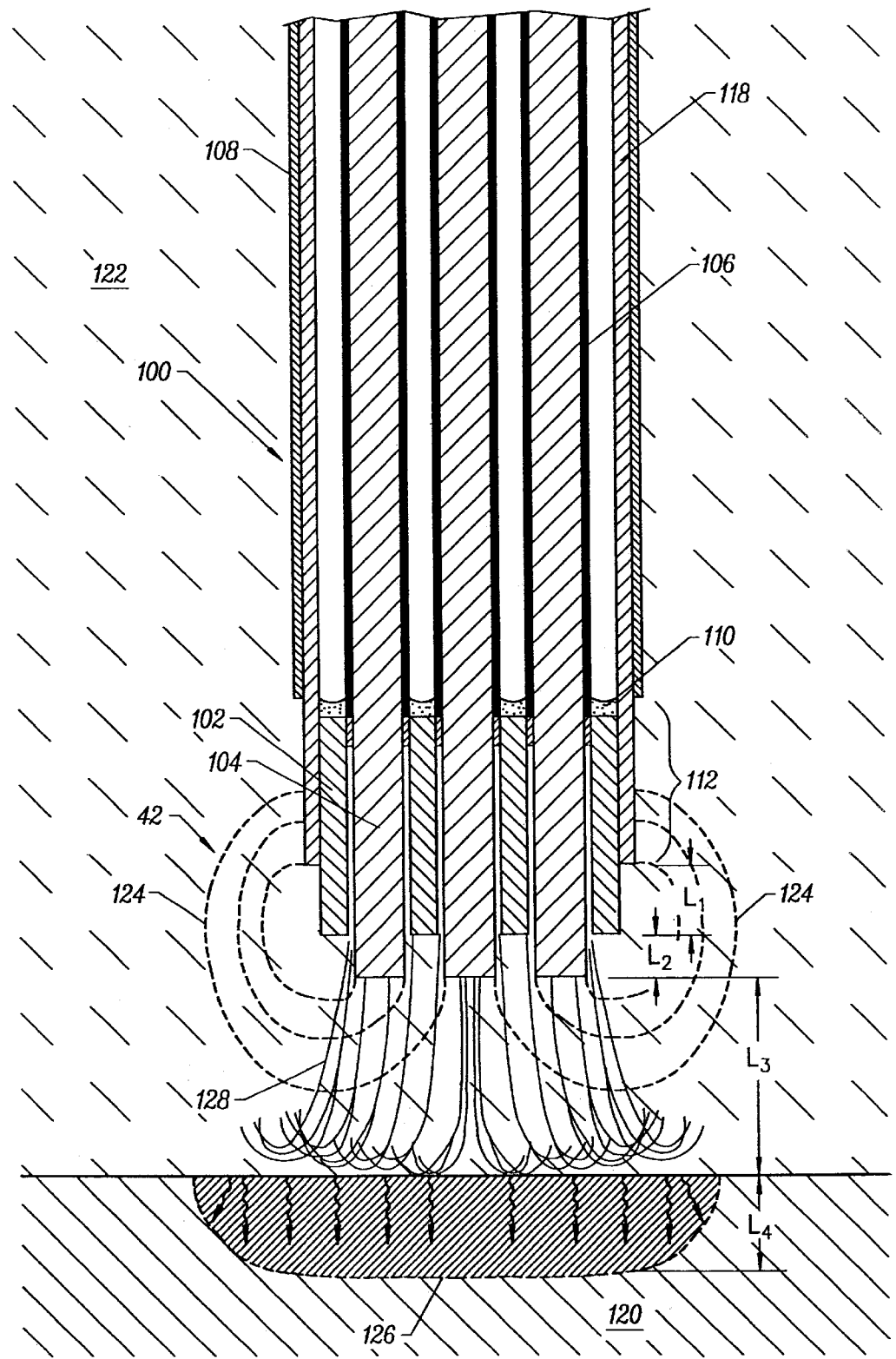
FIG. 13 illustrates another method of contracting tissue with heating fluid according to the present invention.

Referring now to FIG. 13, an alternative method of contracting collagen soft tissue according to the present invention will now be described. As shown, one or more electrode terminals 104 on the distal end of an electrosurgical instrument 100 are positioned adjacent to the target tissue 120. In this method, electrically conducting fluid is delivered to the target site to submerge the target tissue 120 and the distal portion of instrument 100 in the fluid. As discussed above, the fluid may be delivered through instrument 100, or by a separate delivery instrument. When a voltage difference is applied between the electrode terminals 104 and the return electrode 112, electrical current flows between the electrode terminals 104 and the return electrode 112 through the conductive fluid, as shown by current flux lines 124. The current flux lines 124 heat the electrically conductive fluid. Since the electrode terminals are spaced from the tissue 120 (preferably about 0.5 to 10 mm), the current flux lines 124 flow only in the electrically conductive fluid such that little or no current flows in the adjacent tissue 120. By virtue of the current flow through the electrically conductive fluid 122 in the region above the surface of the tissue, heated fluid is caused to flow away from the working end 42 towards the target tissue 120 along heated fluid path 128. Alternatively, the fluid may be delivered past the electrode terminals 104 in a jet of fluid that is delivered onto the target tissue to effect a more define zone of heating. The heated fluid elevates the temperature of the tissue from normal body temperatures (e.g., 37° C.) to temperatures in the range from 55° C. to 85° C., preferably in the range from 60° C. to 70° C.

Figure 14:
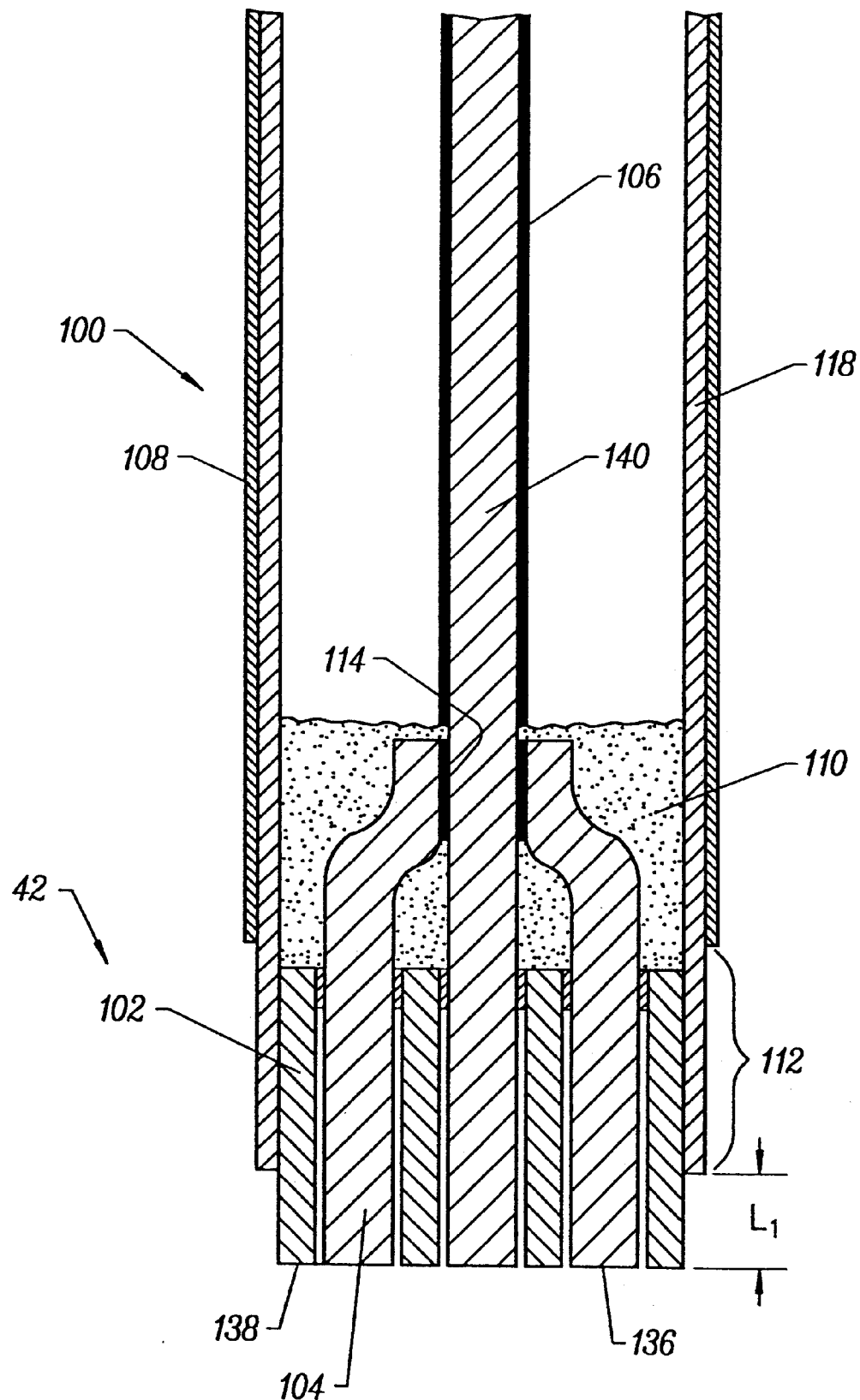
FIG. 14 illustrates another electrosurgical probe with a single active electrode lead.

Still yet another embodiment of the present invention is illustrated in FIG. 14. This embodiment is similar to previous embodiments except that the electrode terminals 104 are joined to a single electrode terminal lead 140 through a low resistance bond 114. By way of example, low resistance bond 114 may be effective through the use of solder, braze, weld, electrically conductive adhesive, and/or crimping active electrode wires 104 within a deformable metal sleeve (not shown). In the configuration shown in FIG. 14, all active electrode leads are maintained at the same potential independent of the current flowing between a particular electrode terminal 104 and the return electrode. This configuration offers the simplicity of requiring only two leads between the generator 10 and the working end 42 of probe 20, viz., one lead for the electrode terminals 104 and one lead for the return electrode.

Referring again to FIG. 7, an advantage of a symmetrical array of electrode terminals 10 is that the loci of current flux lines 124 in tissue 120 is independent of the direction of the translational movement of the electrode array over the surface of the target tissue 120. In contrast, the electrode terminal array 104 in FIG. 8C requires that the translational movement be normal to the major axis of the electrode terminal 104 as illustrated by the preferred translation vector 142.

In the embodiment illustrated in FIGS. 6 and 7, each active electrode 104 can be independently controlled by generator 10 by active or passive current and/or voltage controlling means as fully described in co-pending of PCT International Application, U.S. National Phase Serial No. PCT/US94/05168, and U.S. patent application Ser. Nos. 08/562,332 and 08/485,219, the complete disclosures of which have previously been incorporated herein by reference for all purposes. As described in the referenced co-pending patent applications, the independent control of current and/or voltage applied to each individual electrode terminal 104 provides the benefit of minimizing unwanted heating of either (1) surrounding fluids (e.g., isotonic saline) or (2) non-target tissue (having distinguishably different electrically properties) when the working end 42 is being translated into and out of contact or close proximity with the target tissue (e.g., joint capsular tissue).

Figure 15:
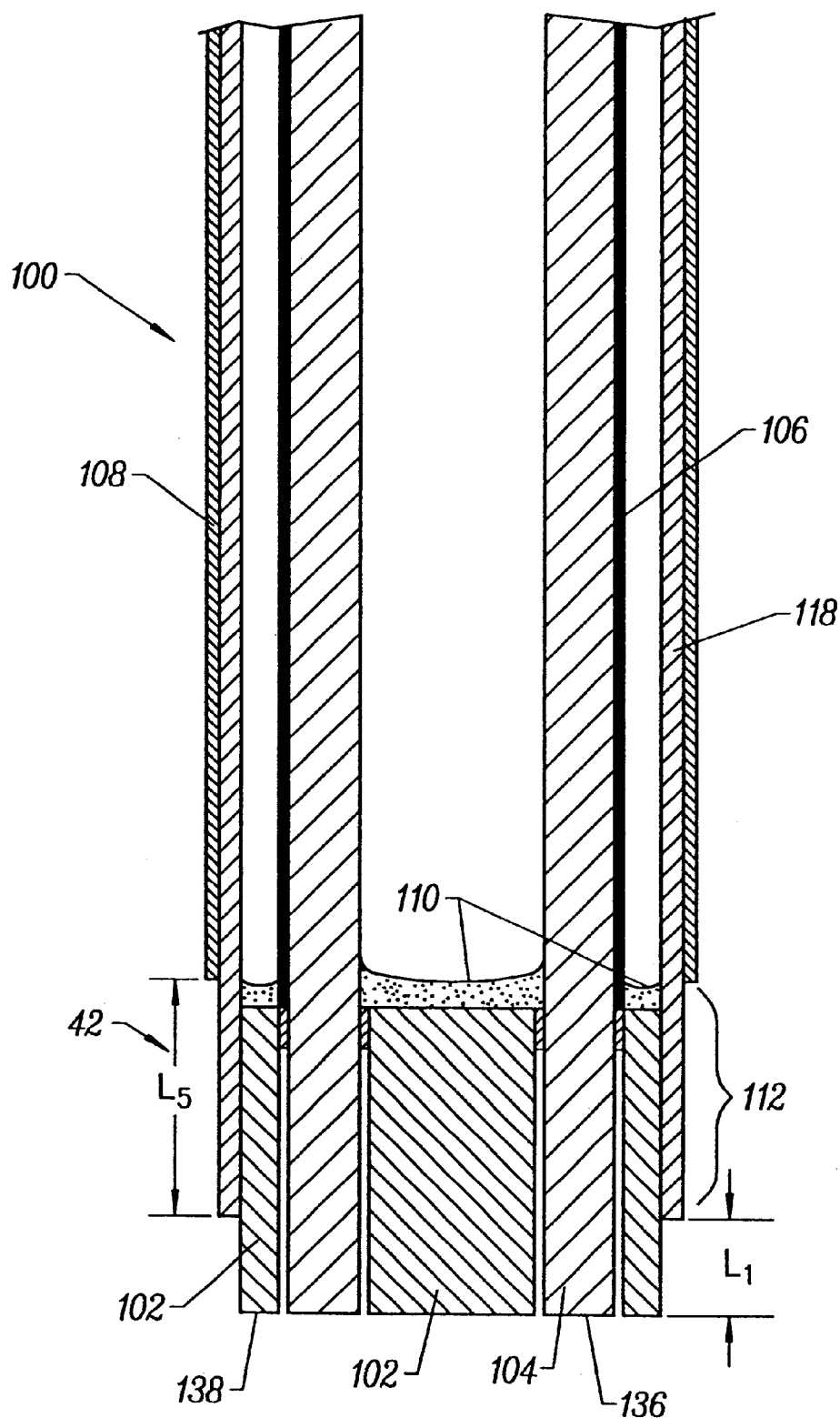
FIGS. 15 and 16 are sectional and end views, respectively, of another electrosurgical probe having a single tubular-shaped electrode.
Figure 16:
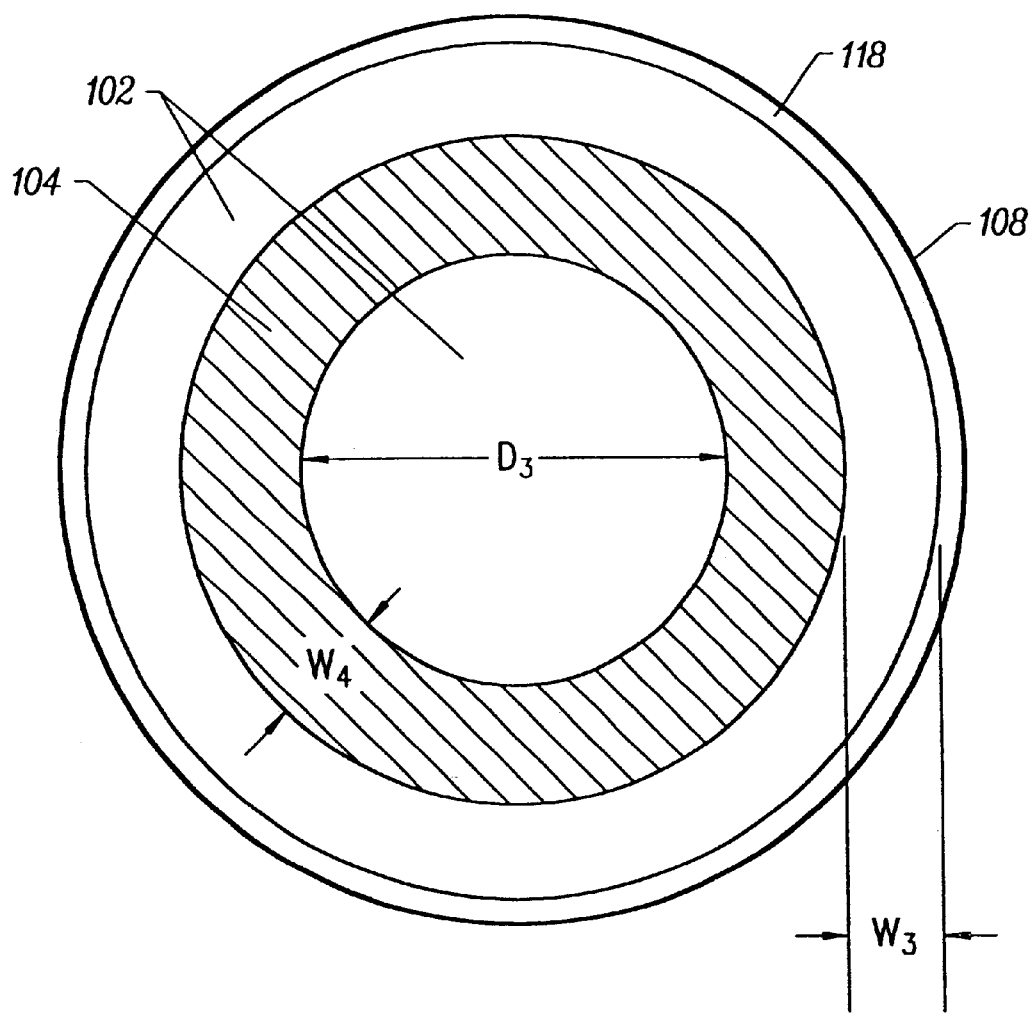

Still yet another embodiment of the present invention is illustrated in FIGS. 15 and 16. In this embodiment, a single tubular-shaped electrode 104 replaces the array of electrode terminals. Other than the configuration and number of electrode terminal(s), all other dimensions and materials of construction remain the same as those described herein above for the first embodiment. The tubular electrode terminal 104 may conventionally be constructed using metal tubing formed by conventional tube drawing (e.g., welded and drawn or seamless drawn) processes. The inside diameter, $D_3$ of the tubular electrode is preferably in the range from 0.3 mm to 5 mm and the thickness of the tubing, $W_4$ is preferably in the range from 0.05 mm to 1 mm and more preferably in the range from 0.1 mm to 0.6 mm.

The distance between the outer perimeter of the electrode terminals 104 and the perimeter of the electrode support member, $W_3$ is preferably in the range from 0.1 mm to 1.5 mm and more preferably in the range from 0.2 mm to 0.75 mm. As discussed above with respect to FIG. 14, this embodiment provides the advantage of requiring only one lead between the electrode terminal 104 at the working end 42 of probe 20 and the generator 10. As before, current flows between electrode terminal 104 and return electrode 112 through the adjacent target tissue 120 and the intervening electrically conductive fluid in the manner described above.

Figure 17:
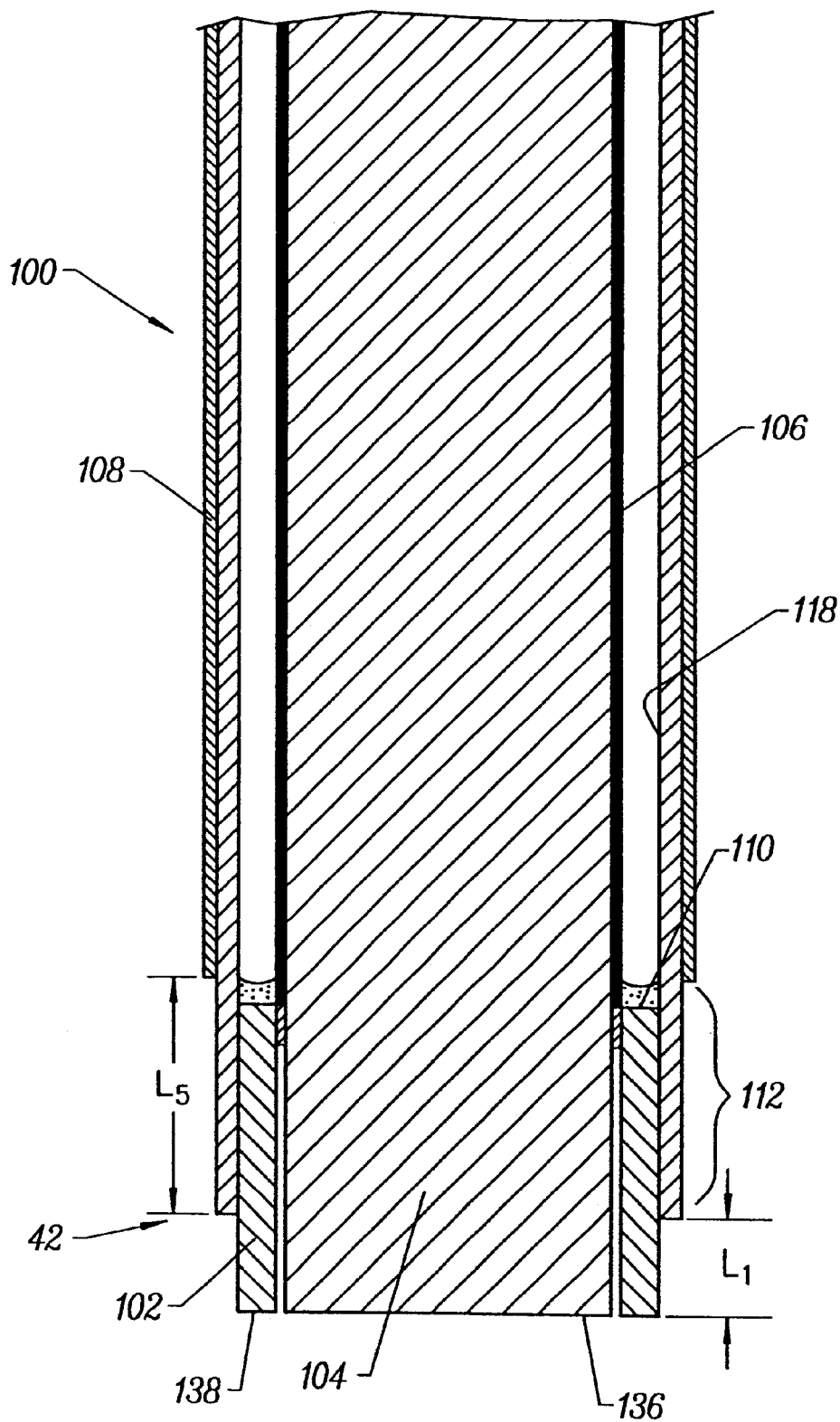
FIGS. 17 and 18 are sectional and end views, respectively, of another electrosurgical probe having a solid cylindrical electrode.
Figure 18:
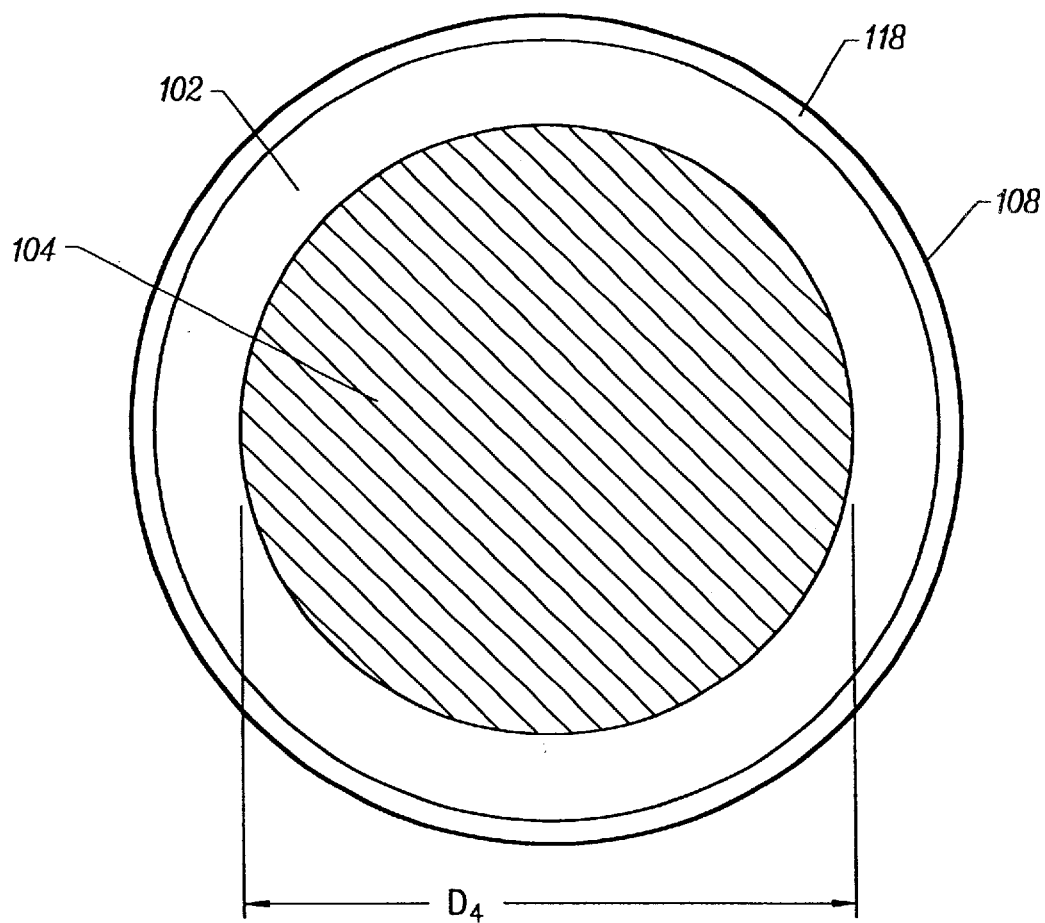

Still yet another embodiment of the present invention is shown in FIGS. 17 and 18. This embodiment is similar to that illustrated in FIGS. 15 and 16 except that the single tubular electrode terminal 104 is replaced with a solid cylindrical electrode whose diameter, $D_4$ is preferably in the range from 0.3 mm to 10 mm. This embodiment offers similar advantages to that described above with respect to the embodiment shown in FIGS. 15 and 16. All other dimensions and materials of construction are similar to those specified with respect to the embodiment shown in FIGS. 6 and 7.

Figure 19:
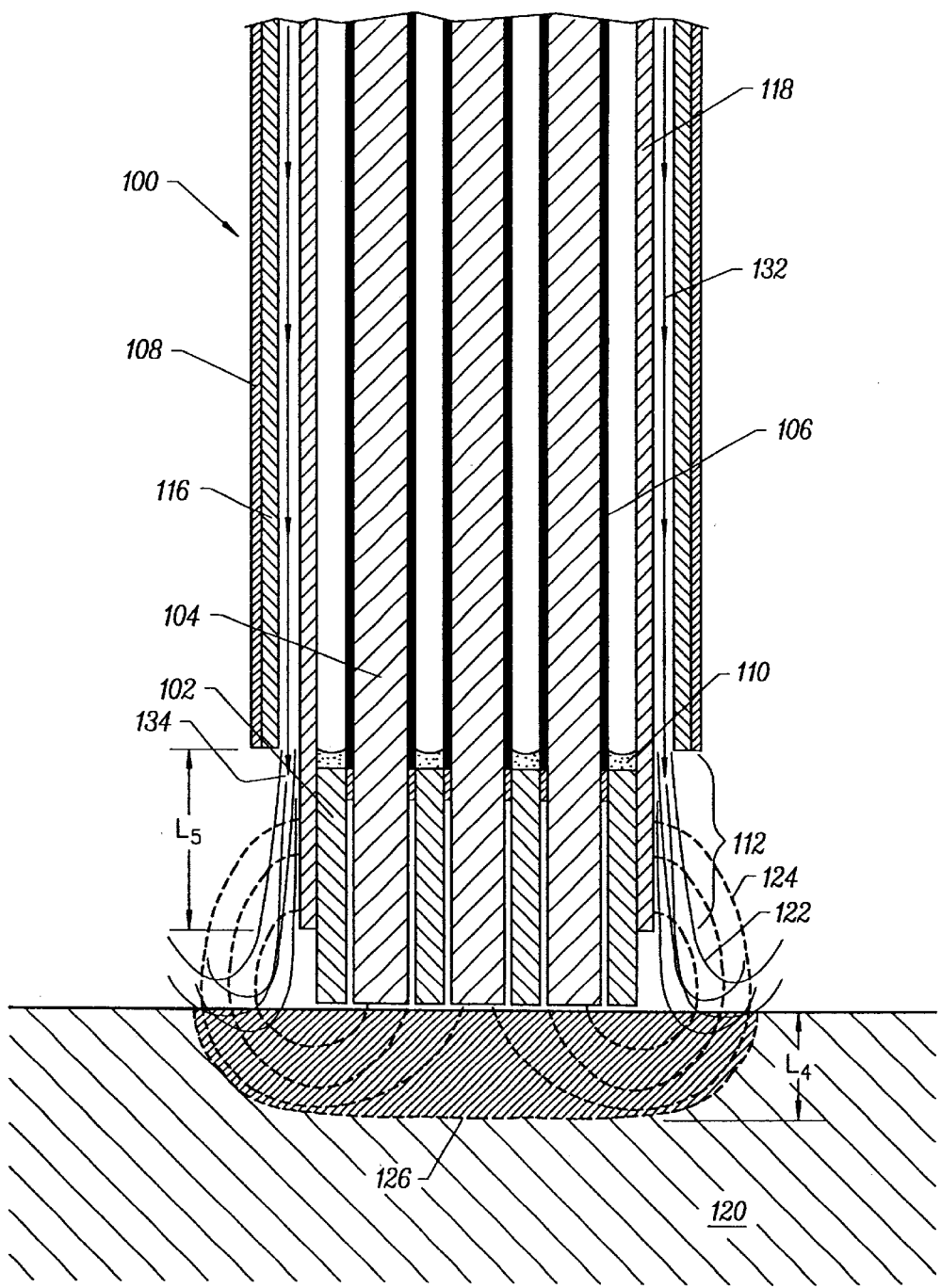
FIGS. 19 and 20 illustrate another embodiment wherein the electrosurgical probe includes a fluid lumen for delivering electrically conductive fluid to the target site.
Figure 20:
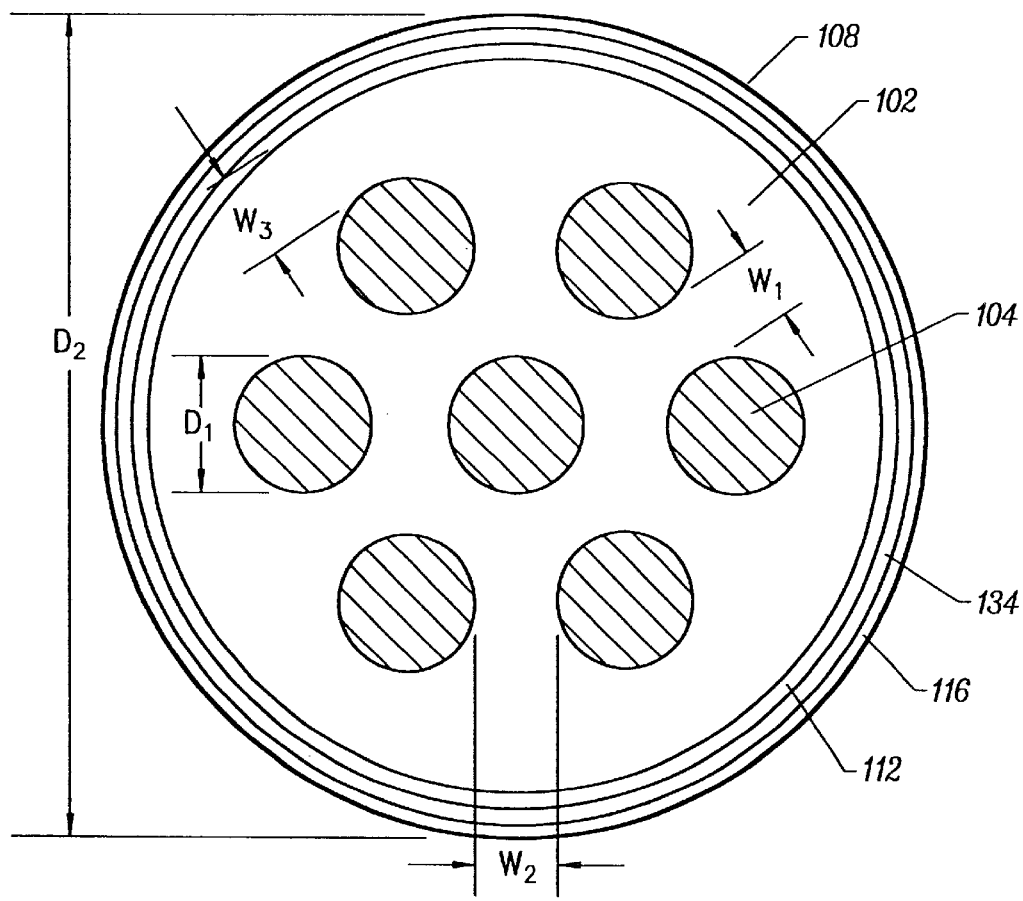

Yet another embodiment of the present invention is illustrated in FIGS. 19 and 20. This embodiment is the same as the first embodiment described in FIGS. 6 and 7 except that a supply channel for the electrically conductive fluid is provided to allow the working end 42 of probe 20 to be used in applications where the volume surrounding the working end 42 of the probe 20 and tissue 120 is not filled with an electrically conductive liquid (e.g., an irrigant fluid compartment surrounding the knee or shoulder joint). As a consequence, the embodiment shown in FIG. 19 can be used on tissue surfaces that are otherwise dry (e.g., the surface of the skin).

As shown in FIGS. 19 and 20, electrically conductive fluid 122 is supplied through an annular space formed between cannula 118 and outer sleeve 116. Outer sleeve 116 may be an electrically insulating material (e.g., polyimide or polyethylene tubing), or a metallic tubular member covered by an electrically insulating sleeve 108 as described above. The electrically conductive fluid is caused to move along flow path 132 and exit the annular flow space at annular orifice 134. As shown in FIG. 19, the application of a voltage difference between the electrode terminal or electrodes 104 and the return electrode 112 causes current flow through the tissue 120 in region 126 and along the stream of electrically conductive fluid 122 to complete the electrical circuit. All other dimensions and materials of construction are the same as defined for the preceding embodiments. This embodiment is particularly useful for therapeutic contraction of collagen underlying the surface of the skin.

Figure 21:
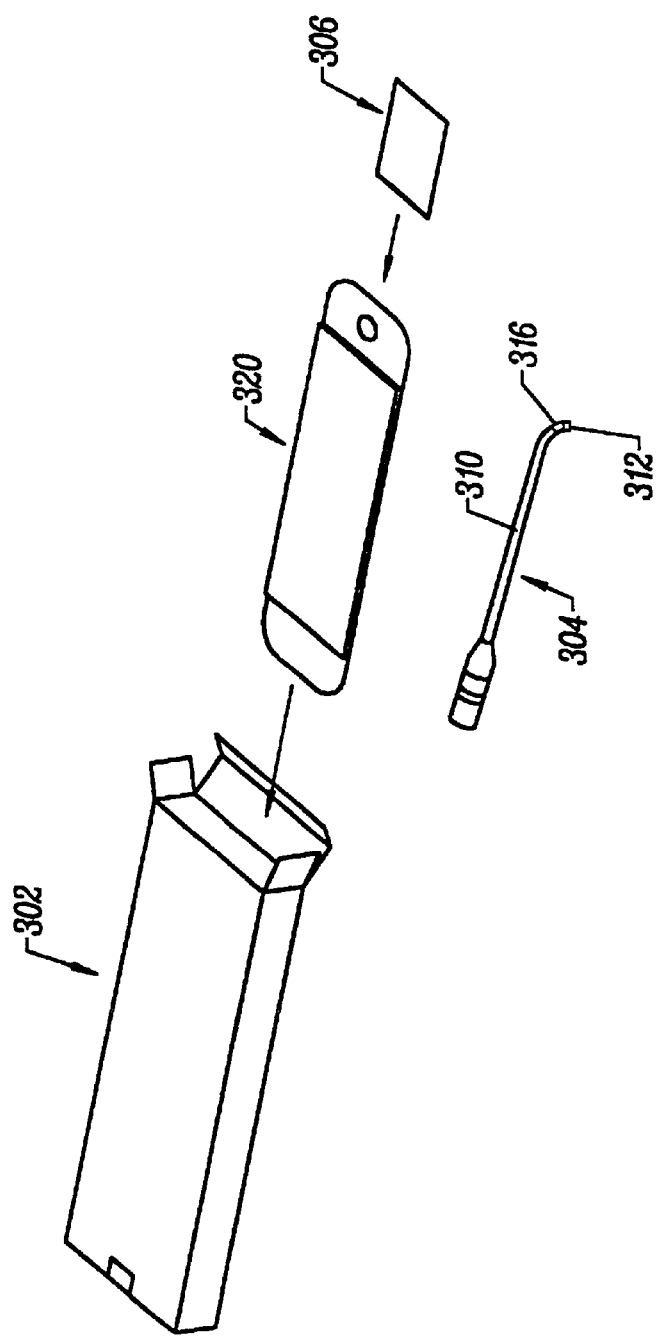
FIG. 21 illustrates a surgical kit for shrinking the collagen fibers of the joint capsular tissue according to the present invention.

Referring now to FIG. 21, a surgical kit 300 for shrinking the collagen fibers of the joint capsular tissue according to the invention will now be described. As shown, surgical kit 300 includes a package 302 for housing a surgical instrument 304, and an instructions for use 306 of instrument 304. Package 302 may comprise any suitable package, such as a box, carton, wrapping, etc. In the exemplary embodiment, kit 300 further includes a sterile wrapping 320 for packaging and storing instrument 304. Instrument 304 includes a shaft 310 having at least one electrode terminal 312 at its distal end, and at least one connector (not shown) extending from electrode terminal 312 to the proximal end of shaft 310. The instrument 304 is generally disposable after a single procedure. Instrument 304 may or may not include a return electrode 316.

The instructions for use 306 generally includes the steps of adjusting a voltage level of a high frequency power supply (not shown) to effect a contraction of the collagen within the soft tissue at the target site, connecting the surgical instrument 304 to the high frequency power supply, positioning the electrode terminal 312 within electrically conductive fluid at or near the soft tissue at the target site, and activating the power supply to induce contraction of the collagen tissue. The voltage level is usually about 30 to 70 volts rms and preferably about 40 to 60 volts rms for surgical instruments having electrode diameters or principal dimensions of about 0.3 to about 0.4 mm and operating frequencies of about 100 to 200 kHz. In the preferred embodiment, the positioning step includes introducing at least a distal portion of the instrument 304 through a portal into a joint.

The instructions for use 306 further includes the instruction of maintaining the instrument 304 in motion during application of RF current to achieve the maximum effect on the target tissue. The amount of thermal energy imparted by the electrode terminals to the tissue (and consequently the temperature of the tissue) will also depend on the time in which the electrodes are held in contact with or in close proximity to the tissue. With the operating frequency and electrode configuration of the present invention, the surgeon should generally move the instrument transversely across the tissue at a relatively slow rate (e.g., usually about 0.1 to 5.0 cm/sec and preferably about 0.2 to 3 cm/sec) in order to ensure that the tissue is heated to a temperature within the target range of 60° C. to 70° C., without applying too much thermal energy to the tissue.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, depending on other conditions, such as the peak-to-peak voltage, electrode diameter, etc., a single electrode terminal may be sufficient to form a heated plume of fluid that induces the contraction of collagen tissue.

Further, the electrode array may include both active and return electrodes. In this embodiment, the active and return electrodes are both located on a distal tissue treatment surface adjacent to each other. The active and return electrode may be located in active/return electrode pairs, or one or more return electrodes may be located on the distal tip together with a plurality of electrically isolated electrode terminals. The proximal return electrode may or may not be employed in these embodiments. For example, if it is desired to maintain the current flux lines around the distal tip of the probe, the proximal return electrode will not be desired.

What is claimed is:

1. A surgical instrument for applying high frequency electrical energy to tissue at a target site comprising:
   a shaft having a proximal end and a distal end;
   an electrically insulating support at or near the distal end of the shaft, the electrically insulating support having a tissue treatment surface, and wherein the electrically insulating support comprises an inorganic material selected from the group consisting essentially of glass, ceramic and lass/ceramics;
   an electrode array comprising at least three electrode terminals at least partially embedded within the electrically insulating support, wherein the electrode terminals are substantially flush with the tissue treatment surface of the electrically insulating support; and
   one or more connectors extending from the electrode terminals to the proximal end of the shaft.

2. The surgical instrument of claim 1 further comprising a return electrode positioned on the shaft proximal to the electrode array.

3. The surgical instrument of claim 1 wherein the electrode terminals are electrically isolated from each other.

4. The surgical instrument of claim 1 further comprising at least five electrode terminals embedded within the electrically insulating support.

5. The surgical instrument of claim 1 wherein the return electrode is a substantially annular band positioned proximal to the electrode array.

6. The surgical instrument of claim 1 wherein the electrode terminals each have a tissue treatment surface substantially flush with the tissue treatment of the electrically insulating support so as to minimize dissociation and breakdown of collagen fibers in the tissue and to minimize ablation of tissue surrounding the collagen fibers.

7. The surgical instrument of claim 6 wherein the tissue treatment surfaces of the electrode terminals each have a surface area less than about 1 mm$^2$.

8. The surgical instrument of claim 6 wherein a distal portion of the shaft is bent such that the electrode terminals have a tissue treatment surface that is non-perpendicular to the longitudinal axis of the shaft.

* * * * *